(12) United States Patent
Carter et al.

(10) Patent No.: US 12,302,813 B2
(45) Date of Patent: May 20, 2025

(54) PLANT POLLINATION CONTROL STRUCTURES

(71) Applicant: PBS International Ltd, Scarborough (GB)

(72) Inventors: Stuart Carter, Scarborough (GB); Derek Paley, Scarborough (GB); Roland Stokes, Scarborough (GB); Hannah Senior, Scarborough (GB); Maggie Temple, Scarborough (GB)

(73) Assignee: PBS International Ltd, Scarborough (GB)

( * ) Notice: Subject to any disclaimer, the term of this patent is extended or adjusted under 35 U.S.C. 154(b) by 243 days.

(21) Appl. No.: 17/638,228

(22) PCT Filed: Aug. 28, 2020

(86) PCT No.: PCT/GB2020/052072
§ 371 (c)(1),
(2) Date: Feb. 25, 2022

(87) PCT Pub. No.: WO2021/038245
PCT Pub. Date: Mar. 4, 2021

(65) Prior Publication Data
US 2022/0312706 A1    Oct. 6, 2022

(30) Foreign Application Priority Data

Aug. 29, 2019 (GB) .................................... 1912432
Jun. 16, 2020 (GB) .................................... 2009135

(51) Int. Cl.
*E04H 15/64*    (2006.01)
*A01G 9/16*    (2006.01)
(Continued)

(52) U.S. Cl.
CPC ............... *A01H 1/027* (2021.01); *A01G 9/16* (2013.01); *A01G 13/21* (2025.01); *A01G 13/27* (2025.01); *E04H 15/644* (2013.01)

(58) Field of Classification Search
CPC .... A01G 13/0206; A01G 9/16; E04H 15/644; A01H 1/027
See application file for complete search history.

(56) References Cited

U.S. PATENT DOCUMENTS 3,424,178 A    1/1969   Yoshimi
4,036,244 A *   7/1977   Huddle ................... E04H 15/40
                                                              52/63
(Continued)

FOREIGN PATENT DOCUMENTS

DE      2145502 A1 *   3/1973
DE      2646050 A1 *   4/1978
(Continued)

OTHER PUBLICATIONS

International Search Report and Written Opinion for PCT/GB2020/052072 mailed Feb. 1, 2021 (15 pages).
(Continued)

*Primary Examiner* — Adriana Figueroa
(74) *Attorney, Agent, or Firm* — Brooks Kushman P.C.

(57) ABSTRACT

A pollination control structure comprises a support; a plurality of support fixings, each support fixing being attached to or integral with the support, and; a barrier member comprising a plurality of barrier member pieces. At least one of the barrier member pieces is releasably attached to at least one of the support fixings by an intermediate fixing. The barrier member piece is releasably attached to the intermediate fixing, and the intermediate fixing is releasably attached to the support fixing.

19 Claims, 12 Drawing Sheets

(51) Int. Cl.
    *A01G 13/21*  (2025.01)
    *A01G 13/27*  (2025.01)
    *A01H 1/02*  (2006.01)

(56) References Cited

U.S. PATENT DOCUMENTS

| | | | | |
|---|---|---|---|---|
| 4,163,303 | A * | 8/1979 | Hanna | E05D 9/00 |
| | | | | 24/444 |
| 4,259,819 | A * | 4/1981 | Wemyss | E04H 15/322 |
| | | | | 52/273 |
| 5,555,681 | A * | 9/1996 | Cawthon | E04B 7/028 |
| | | | | 52/79.5 |
| 5,709,238 | A * | 1/1998 | Mattioli | E04H 15/34 |
| | | | | 135/117 |
| 5,778,613 | A * | 7/1998 | Thomson | E04H 15/64 |
| | | | | 52/273 |
| 6,098,335 | A | 8/2000 | Brown, Jr. | |
| 6,701,948 | B2 * | 3/2004 | Jopp | E04H 15/001 |
| | | | | 135/97 |
| 7,614,415 | B1 | 11/2009 | Wehner | |
| 7,748,162 | B1 | 7/2010 | Necessary et al. | |
| 8,245,464 | B2 * | 8/2012 | Saiz | A01G 9/1415 |
| | | | | 52/75 |
| 8,261,485 | B2 * | 9/2012 | Sauermann | A01G 9/16 |
| | | | | 47/17 |
| 9,598,876 | B1 * | 3/2017 | LaHood | E04H 15/48 |

FOREIGN PATENT DOCUMENTS

| | | | | |
|---|---|---|---|---|
| DE | 3025908 | A1 * | 2/1982 | |
| DE | 3038721 | A1 | 5/1982 | |
| DE | 3824142 | A1 * | 1/1990 | |
| FR | 2638059 | A1 | 4/1990 | |
| GB | 1057247 | A * | 2/1967 | |
| GB | 1600238 | A * | 10/1981 | E04H 15/18 |
| WO | 0104431 | A1 | 1/2001 | |

OTHER PUBLICATIONS

International Preliminary Report on Patentability for PCT/GB2020/052072 prepared Dec. 20, 2021 (71 pages).

* cited by examiner

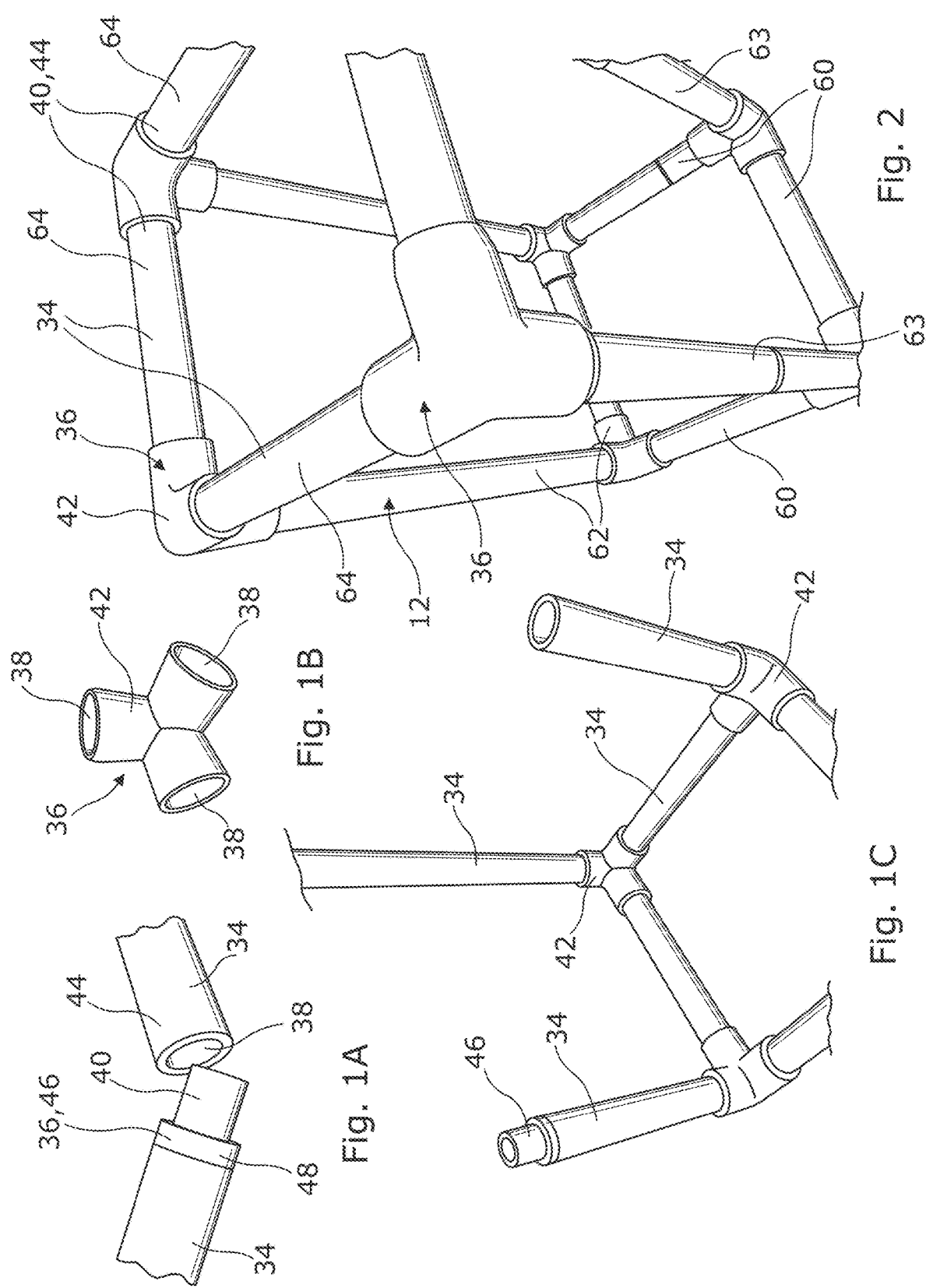

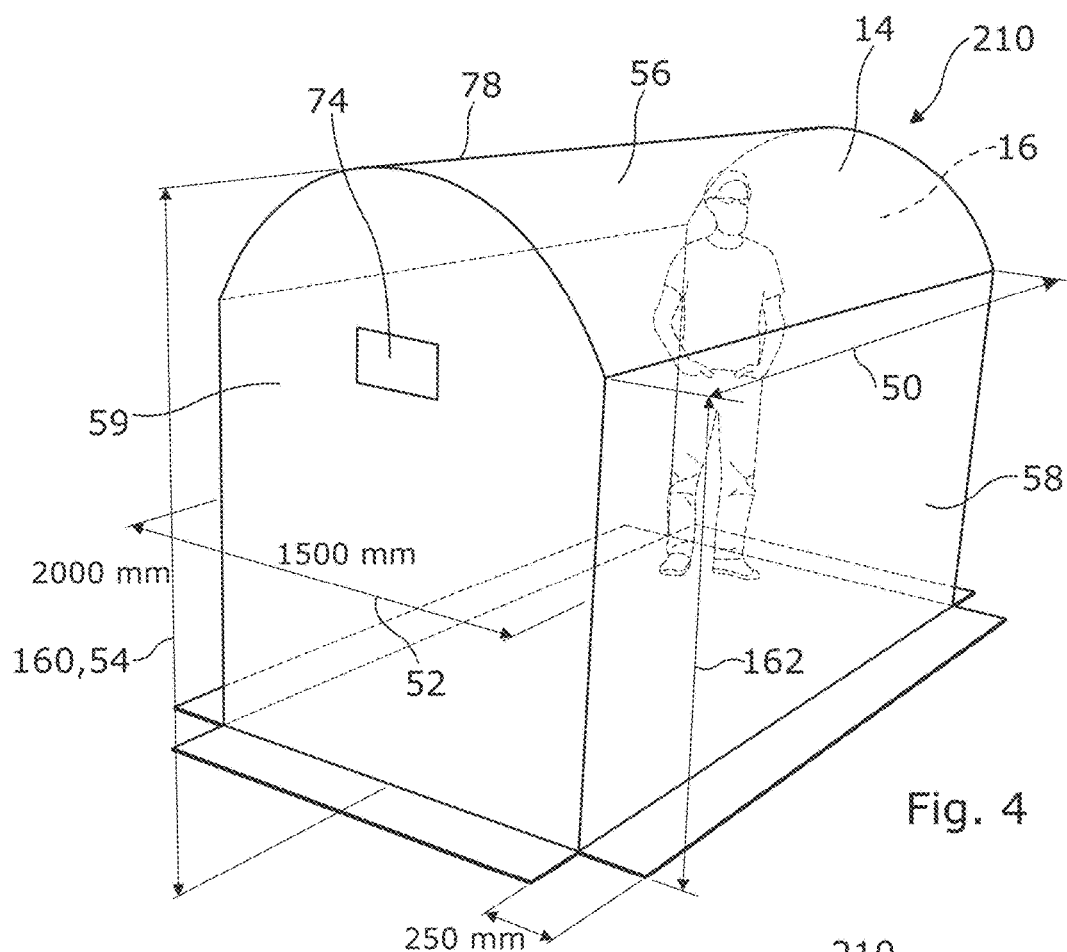
Fig. 4
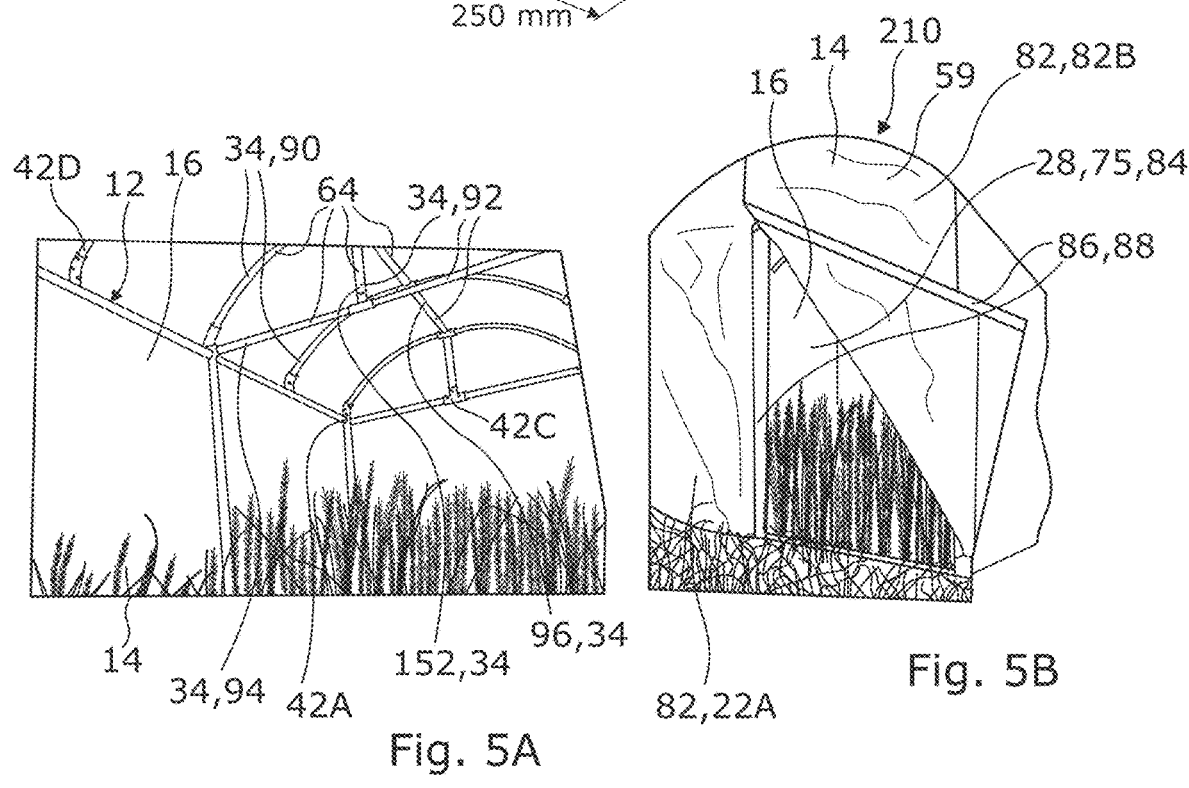
Fig. 5A
Fig. 5B

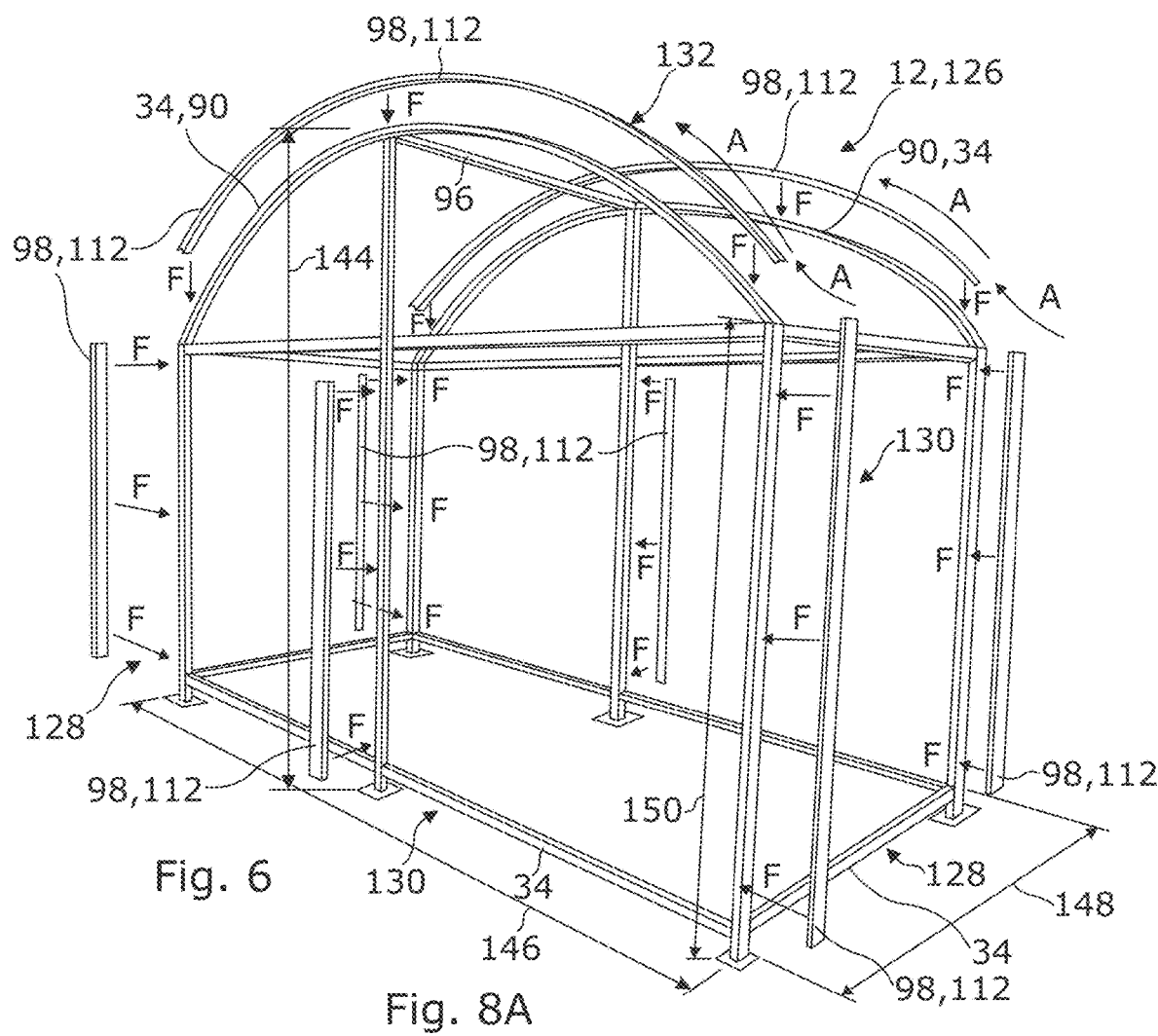
Fig. 6
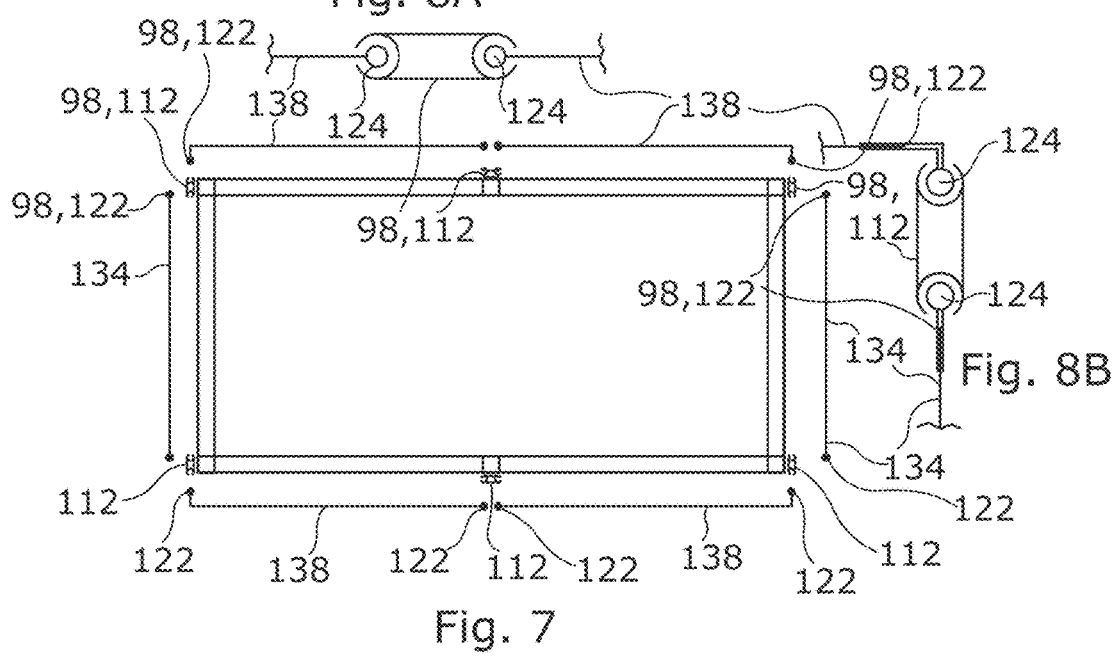
Fig. 8A
Fig. 7
Fig. 8B

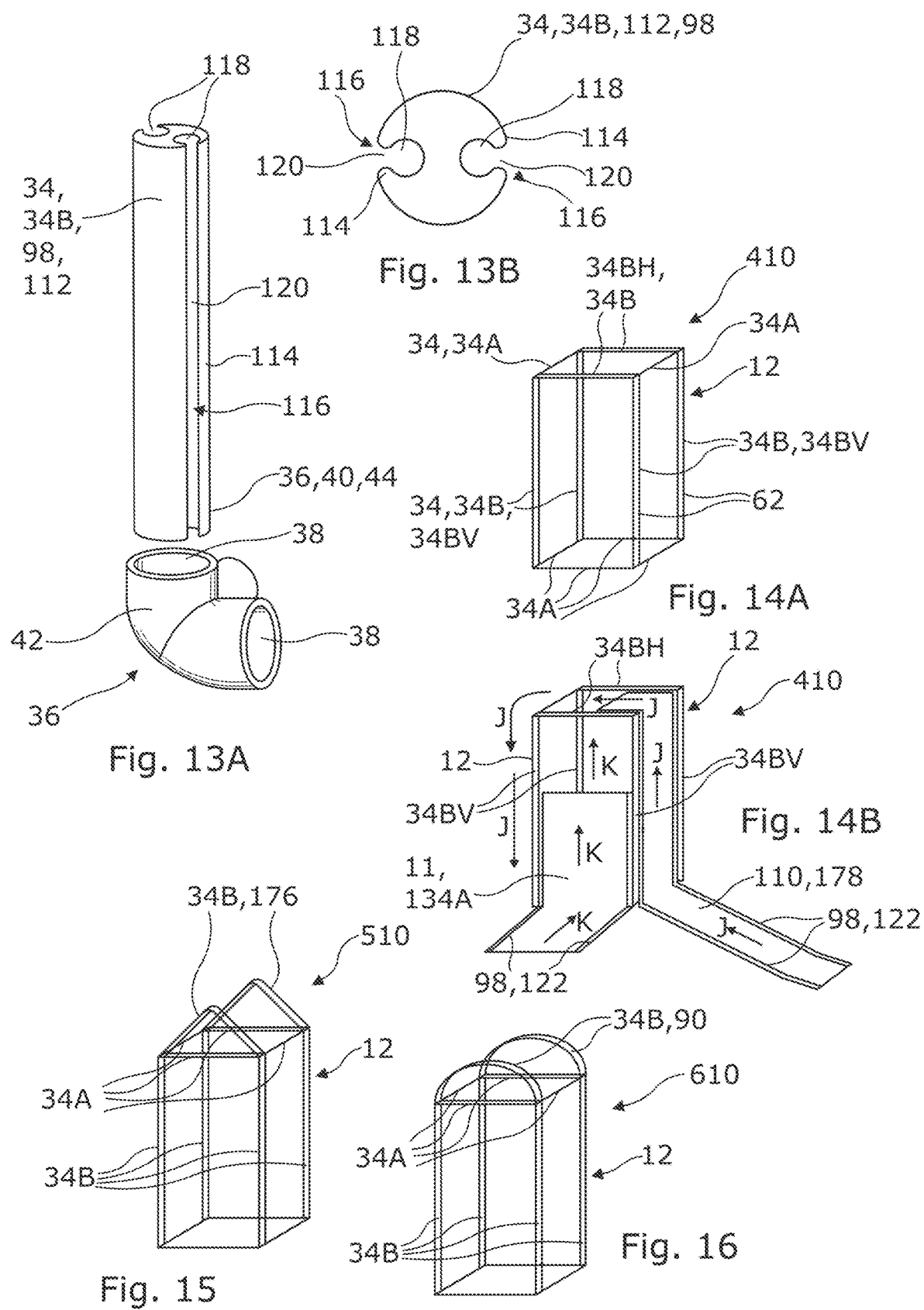

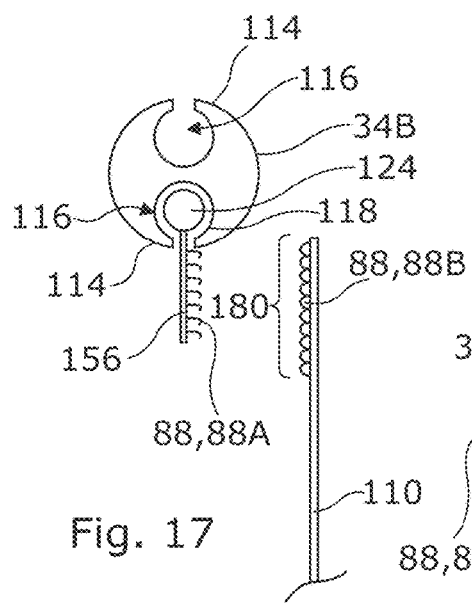
Fig. 17
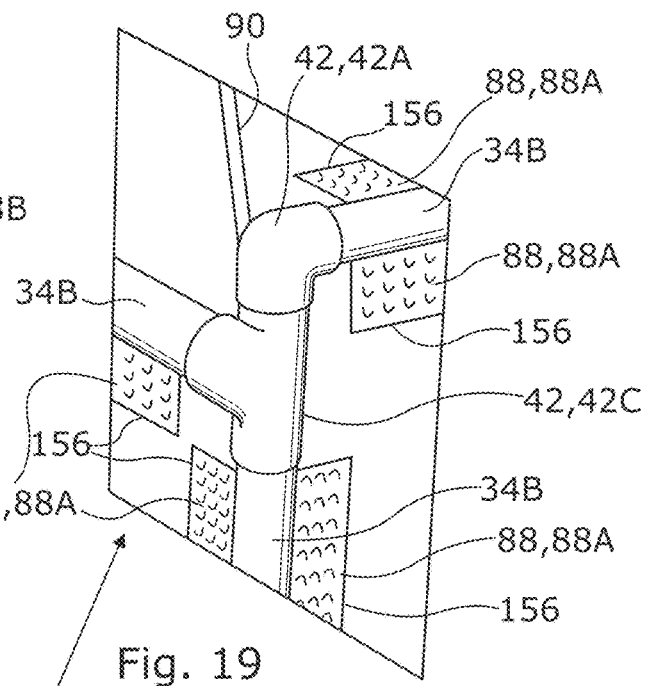
Fig. 19
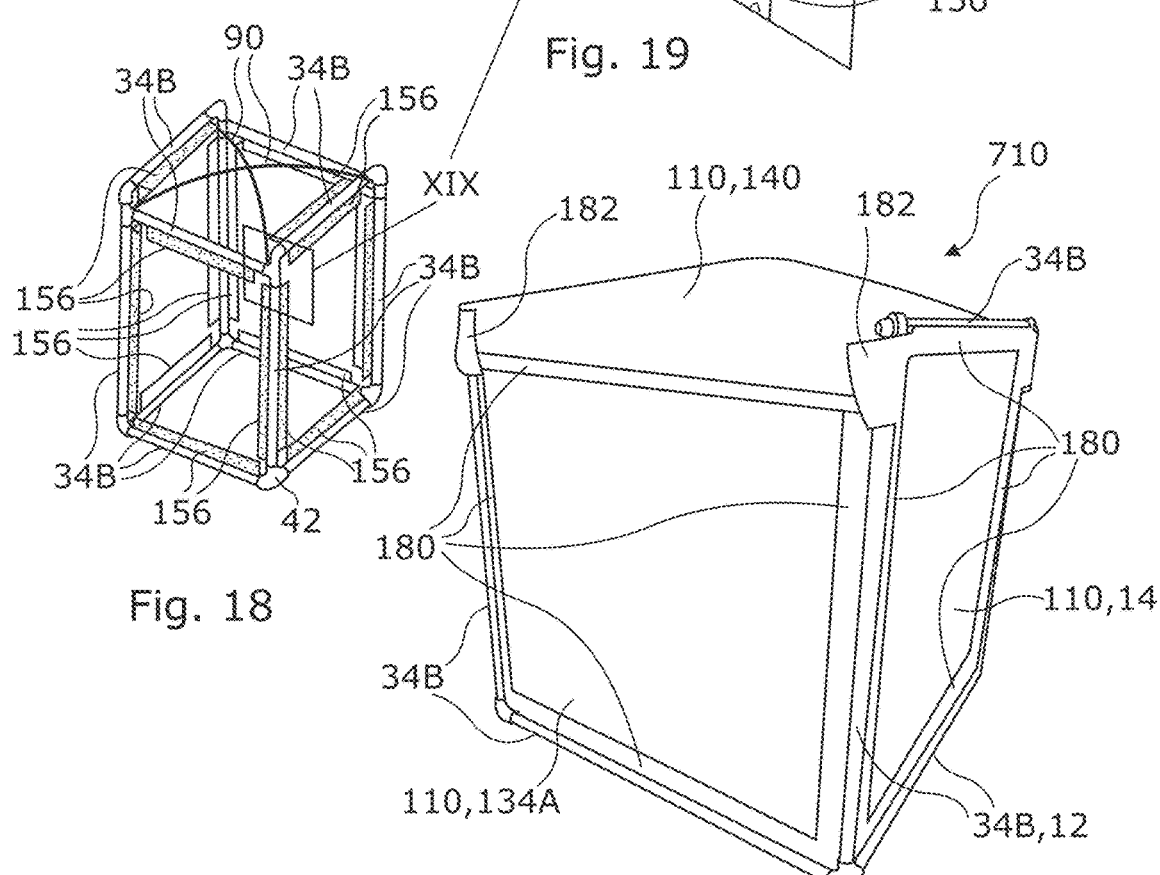
Fig. 18
Fig. 20

PLANT POLLINATION CONTROL STRUCTURES

CROSS-REFERENCE TO RELATED APPLICATIONS

The present application is a U.S. national phase application filed under 35 USC § 371 of international application number PCT/GB2020/052072 filed on Aug. 28, 2020, which claims priority to and all benefits of patent applications filed with the United Kingdom Intellectual Property office as GB1912432.0 filed on Aug. 20, 2019 and GB2009135.1 filed Jun. 16, 2020, all three of which are incorporated herein by reference.

TECHNICAL FIELD

The present disclosure relates to plant pollination control structures.

BACKGROUND

Conventionally, it is known to provide pollination bags to control plant pollination. The bag defines an interior and one or more openings which can be closed or restricted. In use, the bag is located over a reproductive part of the plant to provide a barrier to the movement of pollen. However the bag is formed of a material which is relatively flexible and can be relatively easily deformed so that plant damage can occur if the material is moved (e.g., by a person, an animal or by weather conditions). Also, similarly, damage can occur when fitting and removing the bag. In some situations, pollination control is required over a relatively large plant or an area of planting which can be inefficient with relatively small bags.

In this specification, the terms inner, outer, inwardly and outwardly, when used in relation to the structure, are used with respect to the interior, which is inward of the structure, and the terms upward and downward are used in relation to the in use orientation of the structure, in which downward means down towards the ground.

SUMMARY OF THE DISCLOSURE

According to a first aspect of the disclosure, there is provided a pollination control structure comprising a support, a plurality of support fixings and a barrier member. Each support fixing is attached to or integral with the support. The barrier member comprises a plurality of barrier member pieces. At least one of the barrier member pieces is fixed to at least one of the support fixings by an intermediate fixing, also referred to as a barrier member fixing, that offsets the barrier member piece from the support fixing, wherein the at least one barrier member piece is releasably attached to the intermediate fixing, and the intermediate fixing is releasably attached to the support fixing. The barrier member pieces are suspended entirely within openings defined between the support fixings and are arranged such that they do not overlap the support.

Providing an intermediate fixing between a barrier member piece and the support is advantageous, because it allows for the barrier member piece to be removed from the support without having to adjust or alter the engagement between the intermediate fixing and the support. The intermediate fixing allows the support to be customised for releasable attachment to a barrier member piece, without the support members themselves being specifically designed for this purpose.

At least one of the barrier member pieces may comprise at least one releasable fastening defined along at least one edge of the barrier member piece for releasably attaching the barrier member piece to the intermediate fixing.

In this way, an edge of at least one barrier member piece can be pulled away from the support, for example to provide an access opening in the form of a door or window.

In some embodiments, each edge of some or all of the barrier member pieces includes a releasable fastening. In this way, the barrier member piece can be fully removed from the support when required, for example to be repaired and/or replaced. The releasable fastenings may extend along substantially the entire length of the edge region on which they are provided to provide a well-sealed and thus well controlled environment in the interior of the pollination control structure.

In the assembled structure, the releasable fastenings may be positioned adjacent the support fixings. The barrier member pieces may be suspended entirely within openings defined between the support fixings that make up the support. In that case, the barrier member pieces do not overlie, overlap, or otherwise contact the support fixings.

The intermediate fixings offset the barrier member pieces from the support fixings, so as to avoid abrasion caused by rubbing of the barrier member pieces against the support. The barrier member pieces may comprise a non-woven material. The intermediate fixings may comprise a stronger, more durable material than the barrier member pieces.

The releasable fastenings may comprise hook or loop material for releasably engaging with complementary hook or loop material of the intermediate fixing. When this type of fastening is provided along each edge of a barrier member piece, the barrier member piece may be removed from the support simply by pulling the piece away from the support.

At least one of the support fixings may comprise a channel and at least one of the intermediate fixings may comprise a bead formation that slidably locates in the channel to releasably attach the intermediate fixing to the support fixing. In this way, the releasable attachment between the intermediate fixing and the barrier member piece may be easier to disengage than the releasable attachment between the intermediate fixing and the support. In some cases, some or all of the intermediate fixings may be attached to the support on assembly of the support, and may remain attached to the support up until the support is disassembled e.g., prior to storage of the structure or reassembly of the structure in another location or arrangement. Some or all of the barrier member pieces may be detached from the intermediate fixing to be repaired or replaced one or more times between assembly and disassembly of the structure. For example, when a panel is damaged or worn, a user may simply detach the barrier member piece from the structure, whilst leaving the intermediate fixing in place and ready for attachment of a new (or repaired) barrier member piece.

At least one of the barrier member pieces may comprise a non-woven material. At least one of the barrier members pieces may comprise a different material from at least one other barrier member piece. In this way, different materials can be used for different parts of the barrier member. This is useful because it may be beneficial for some parts of the barrier member to be formed of a tougher, more robust material, for example, and for other parts of the barrier member to be formed of a more fragile material (e.g., with better or specific properties for pollination control for a given situation).

In embodiments in which some or all of the barrier member pieces are formed of different materials, it is especially advantageous that the system allows for easy removal and replacement of individual panels or pieces of barrier member. This is because different barrier member pieces may be replaced at different intervals such that, for example, more fragile barrier member pieces can be replaced more frequently than tougher more durable barrier member pieces. This saves on materials and costs, as parts of the barrier member which are not damaged or worn need not be replaced simply because another area of the barrier member is damaged or worn.

At least one of the barrier member pieces may comprise a skirt extension for contacting a ground surface on which the structure is installed in a substantially continuous contact line around an interior of the structure. Weighting means may be provided on top of, within, or integral with the skirt extensions when the structure is assembled/installed on the ground surface. In this way, the skirt extensions help to ensure that the interior of the pollination control structure is fully enclosed, and that pollen cannot enter in an uncontrolled manner through, for example, gaps between the base of the support and the ground on which the structure is assembled. This may be especially important when the structure is installed on an uneven ground surface where significant gaps may exist between the base of the support and the ground surface. The weighting means help to improve the contact between the skirt extensions and the ground surface, protect against the skirt extensions being blown up in windy weather conditions to expose gaps between the structure and the ground surface, and act as an additional anchoring means for the structure.

The support may comprise a plurality of support members held together by connection arrangements that are arranged to permit assembly, disassembly and re-assembly of the support. Each support fixing may be attached to or integral with a support member of the support.

Each support member may comprise four generally rectangular side faces and two generally square end faces. Each side face may comprise a channel for receiving an intermediate fixing. Each connection arrangement may comprise a substantially flat plate having three attachment portions arranged such that, in an assembled condition, support members attached at the attachment portions are angled at 90 degrees to each other.

In another aspect, the disclosure resides in a method of assembling a pollination control structure comprising a support and a barrier member, the support comprising a plurality or support members and the barrier member comprising a plurality of barrier member pieces. The method comprises: assembling the support from the support members; attaching at least one support fixing to the support and/or forming at least one support fixing integrally with the support; attaching at least one intermediate fixing to the support using a releasable fastening; and attaching at least one of the barrier member pieces to at least one of the intermediate fixings using a releasable fastening to suspend the barrier member piece entirely within an opening defined between the support fixings such that the barrier member piece does not overlap the support.

The disclosure also resides in a kit of parts for assembling a pollination control structure, the kit of parts comprising: a plurality of support members; a plurality of barrier member pieces; and at least one intermediate fixing configured for releasable attachment to at least one of the barrier member pieces and at least one of the support members, and configured to offset the barrier member piece from the support member to suspend the barrier member piece entirely within an opening defined between support members such that the barrier member piece does not overlap the support.

In another aspect, the disclosure resides in a pollination control structure comprising a barrier member and a support that together define an enclosure, wherein the barrier member is supported by the support and comprises at least one barrier member piece comprising a non-woven material.

Non-woven material is relatively fragile compared to other materials which may be used for pollination control structures, such as mesh or plastic. However, non-woven material may have significantly better pollination control properties for certain situations, e.g. when used with certain types of plant.

The or each barrier member piece may be releasably fixed to the support. The or each barrier member piece may have a length that is less than or equal to 2 metres and a width that is less than or equal to 2 metres.

Fixing the barrier member with respect to the support, rather than simply providing the barrier member as a cover that sits on/over the support, reduces abrasion between the barrier member and the support and enables more fragile materials, e.g. non-woven materials, to be used for the barrier member than would otherwise be possible. This is useful because it allows the barrier member material to be chosen based, to a greater extent, on its pollination control properties, rather than on its strength, because the likelihood of damage and excessive wear is reduced.

Limiting the dimensions of the barrier member pieces enables more fragile materials to be used than would be possible for larger barrier member pieces, which would be exposed to more wind pressure in use. It has been found that relatively fragile non-woven materials can withstand higher wind pressures relatively well when the dimensions of the barrier member pieces do not exceed 2 metres×2 metres.

Thus, by providing the barrier member in pieces or panels of limited dimension and fixing each piece with respect to the support, the amount of wear and likelihood of damage (e.g. caused by stress on the material caused by windy weather) to the barrier member pieces is reduced, thus allowing a relatively fragile non-woven material to be used for some or all of the barrier member.

At least one of the barrier member pieces may be formed of a different material from at least one other barrier member piece.

At least one of the barrier member pieces may comprise a skirt extension for contacting a ground surface on which the structure is assembled or installed in a substantially continuous contact line around an interior of the structure when the structure is assembled or installed on the ground surface. In this case, the skirt extension may be releasably attached to, and extend from, a support member that defines at least part of a base of the structure. Weighting means may be provided on top of, within, or integral with the skirt extensions when the structure is assembled or installed on the ground surface.

The support may comprise a plurality of body support members and a plurality of roof support members. The body support members may define side and end wall parts of the support, and possibly a base part, and may be relatively rigid to provide a sturdy and robust frame for the pollination control structure. The roof support members may define a roof part of the support. At least one of the roof support members may be relatively flexible, and may specifically be more flexible than the body support members. Providing roof support members having some flexibility allows for a degree of movement of the roof in high winds, for example, thereby removing some of the pressure on the flexible barrier material in this scenario.

In some examples, the relatively flexible roof support members may be curved, so as to advantageously direct wind up and over the structure to again help to reduce the pressure on the barrier member material during windy weather conditions.

At least one of the barrier member pieces may be releasably fixed to the support by an intermediate fixing that slidably locates in a channel of the support to releasably attach the barrier member piece to the support. The barrier member piece may be releasably attached to the intermediate fixing.

According to another aspect of the present disclosure, there is provided a plant pollination control structure, the structure including a relatively rigid support and a relatively flexible barrier member, the barrier member being supported by the support, the barrier member defining an interior.

Possibly, the support is located in the interior.

Possibly, the structure is arranged to substantially prevent the passage of particles such as pollen into the interior.

Possibly, in use, the support is free standing, and may be free standing independent of the barrier member. Possibly, in use, the support locates on a ground surface.

Possibly, the barrier member is not free standing. Possibly, in use, the barrier member contacts the ground surface in a substantially continuous contact line around the interior. Possibly, in use, the barrier member and the ground surface together form a substantially continuous enclosure around the interior.

Possibly, in use in an installed condition, a part of a plant is located in the interior, and another part of the plant may be located in the ground surface.

Possibly, the barrier member defines an opening to permit access to the interior.

Possibly, the opening is a door opening or a window opening.

Possibly, the barrier member includes a window area, which may be formed of transparent material to enable viewing of the interior.

Possibly, the barrier member includes a closure arrangement which is movable between an open condition in which the closure arrangement permits access to the interior and a restricted condition in which the closure arrangement restricts or prevents access to the interior through the opening.

Possibly, the barrier member comprises a material, which may be non-woven and may comprise a synthetic polymer, which may comprise one or more of polyester, polypropylene and/or polyvinylchloride. Possibly, the material comprises a mesh.

Possibly, the support is formed of a plastics material and may be formed by moulding. Possibly, the support is formed of a metal material, possibly steel or aluminium, or a combination of plastics and metal.

Possibly, the support includes a plurality of support members, which are held together by connection arrangements. Possibly, the connection arrangements are arranged to permit assembly, disassembly and re-assembly of the support, and may permit assembly, disassembly and re-assembly without the use of tools, or without the use of specialist tools, and/or by unskilled operatives. Possibly, the support members and the connection arrangements are held together by push fit action and may be secured by locking arrangements which may comprise pins, screws or similar.

Possibly, one of the support members or the connection arrangements defines a socket recess and the other of the support members or the connection arrangements includes a projecting part which, in the assembled condition, may be receivable in the socket recess.

Possibly, the support members are elongate.

Possibly, the connection arrangements comprise corner joint connectors, each of which may define a plurality of the socket recesses, which may be angled relative to each other, and may be angled at 90° relative to each other.

Possibly, each support member includes one or more of the projecting parts, each of which may comprise an end of the support member and which, in the assembled condition, may be received in one of the socket recesses of one of the corner joint connectors.

Possibly, the connection arrangements comprise a straight connector, which may connect two of the support members together in line. Possibly, the straight connector comprises a body and two of the projecting parts which extend in opposite directions from the body.

Possibly, each support member defines one socket recess at each end, in which, in use, one of the straight connector projecting parts is receivable in the assembled condition.

Possibly, each support member is tubular and may be hollow, possibly in the form of a pipe. In some embodiments, at least some of the support members that define a roof of the structure take the form of hollow plastic pipes or piping, for example medium density polyethylene (MDPE) water piping. This provides the roof of the structure with a degree of flexibility that allows for some movement of the roof, e.g. in windy weather conditions. This is useful to reduce the pressure felt by the barrier member in such conditions.

Possibly, the support members are circular in cross-section. Possibly, the connection arrangements are rounded.

Possibly, the structure has a length, a width and a height.

Possibly, the structure height is greater than its width and may be greater than its length. Possibly, the width and the length are substantially the same.

Possibly, the structure has a plurality of horizontal cross-sectional interior areas at different distances up its height. Possibly, the horizontal cross-sectional areas are substantially the same at all of the distances up the height.

Possibly, the structure comprises a roof, two side walls and two end walls. Possibly, the structure does not comprise a floor.

Possibly, the horizontal cross-sectional areas are substantially the same at all of the distances up the height, up to the top of the side walls.

Possibly, the roof is substantially planar, and in the installed condition may be substantially horizontal. Possibly, all of the side walls and the end walls are substantially the same size. Possibly, all of the side walls and the end walls are substantially planar and in the installed condition may extend substantially vertically.

Possibly, the support comprises a base part, side wall parts, end wall parts and a roof part. Possibly, each of the base part, the side and end wall parts and the roof part is substantially planar. Possibly, the base part and the roof part each comprise four corner joint connectors with four equal lengths of support members extending therebetween. Possibly, the side and end wall parts comprise four equal lengths of support members extending between the corner joint connectors of the base part and the roof part. Possibly, all of the support members are straight.

Possibly, the barrier member comprises a roof part and side and end wall parts, which may locate against or alongside, respectively, the roof part and the side and the end wall parts of the support.

Possibly, the barrier member includes securing features to secure the structure to the ground surface in the installed condition. Possibly, the securing features comprise skirt extensions, which may extend outwardly from the side and end wall parts, possibly from a lower edge of each of the side and end wall parts, possibly at the level of the base part, possibly formed of the same material as the barrier member, possibly formed integrally as part of the barrier member.

Possibly, one of the side or end wall parts defines a window opening, through which, in use in the installed condition, a reproductive part of a plant located in the interior may be accessible and/or through which pollen may be introduced to the interior.

Possibly, the barrier member is formed to a shape to fit over the support and may be pre-formed to the shape. Possibly, the pre-formed shape is in the form of a cuboid.

Possibly, in a pre-assembly condition, the barrier member is formed of flat sheet material. Possibly, the sheet material is formed into a bag, which may have a single upper edge with two upper corners and two lower open edges which define an opening.

Possibly, in the installed condition, the bag is folded and each of the two upper corners may be fastened by a fastening to a different one of the barrier member side wall parts.

Possibly, the structure defines a floor opening, through which, in use in moving to an installed condition, a plant or plant part passes to locate in the interior in the installed condition.

Possibly, in use, in moving to the installed condition, the structure is located over a plant, which may be rooted in a ground surface material.

Possibly, in use, in moving to the installed condition, the support is firstly located over the plant and then the barrier member may be located on the support, over the plant.

Possibly, the barrier member is formed to the shape to fit over the support in situ.

Possibly, the barrier member is provided as a single piece and formed from a single piece of material.

Possibly, in the assembled condition, the structure height is no more than 1.5 m, and desirably no more than 1.3 m, possibly no less than 0.9 m and desirably no less than 1.1 m.

Possibly, in the assembled condition, the structure width and/or the structure length is no more than 1.5 m, and desirably no more than 1.0 m, possibly no less than 0.5 m and desirably no less than 0.75 m.

Possibly, the barrier member is not fixed to the support, but may be held in position by virtue of its shape and fit to the support, and possibly by the securing features.

Possibly, the structure roof includes an apex line, which may be aligned parallel to the structure length.

Possibly, the structure includes a pair of side walls and a pair of end walls.

Possibly, the structure roof is curved and may be curved convexly from top of the side walls to the apex line.

Possibly, the end walls extend upwardly to the apex line.

Possibly, one of the side walls or the end walls defines the window opening.

Possibly, one of the side walls or, more desirably, one of the end walls, comprises an opening wall which may be arranged to provide a person access opening to permit access for a person to the interior. Possibly, the opening wall includes a pair of parts which may be movable between a closed condition and an open condition to provide the person access opening. Possibly, the opening wall includes a securing arrangement to secure the opening wall parts in the closed condition. The securing arrangement may comprise a hook and loop (or fleece) fastening, which may be releasable, and may extend substantially a greater portion of, or the whole, height of the respective side or end wall, and may extend substantially the whole height of the structure.

Possibly, the roof support part includes curved roof support members and may include one or more lines of straight support members. The straight support members may comprise cross members which extend across the interior; may include apex support members which substantially extend along the apex line; and may include roof bracing members which extend from the cross members upwardly to the apex support members.

Possibly, the straight support members are provided in a module length, which may be 1500 mm, and which length may determine the width of the structure, possibly the length of the structure (which may comprise more than one module length) and possibly the height of the structure side walls.

Possibly, the structure has an apex height, a side wall height, a width and a length.

Possibly, the structure has a length which is greater than its apex height, which may be greater than its width, which is substantially the same as its side wall height.

Possibly, the structure length is no more than 3.3 m, and desirably no more than 3.1 m, possibly no less than 2.7 m and desirably no less than 2.9 m.

Possibly, the apex height is no more than 2.3 m, and desirably no more than 2.1 m, possibly no less than 1.7 m and desirably no less than 1.9 m.

Possibly, the width and/or the side wall height is no more than 1.8 m, and desirably no more than 1.6 m, possibly no less than 1.2 m and desirably no less than 1.4 m.

Possibly, the structure includes a barrier member fixing arrangement to fix the barrier member to the support. Possibly, the barrier member comprises a plurality of barrier member pieces, which may be separate from each other, each of which is fixed, possibly separately, to the support.

Possibly, the barrier member fixing arrangement includes at least one support fixing, which, in the assembled condition, may be fastened to the support by fasteners such as bolts or screws. Possibly, the or each support fixing is elongate and may fastened to one of the support members and may extend substantially a greater part of the length of the respective support member.

Possibly, each support fixing comprises a channelling formation, which may be elongate. Each channelling formation may extend the full length of the respective support fixing.

Possibly, the channelling formation defines a channel which may extend along the full length of the channelling formation. Possibly, each channel comprises a bore which extends along the length of the channel and may comprise a slot opening which also extends along the length of the channel and extends laterally outwardly to permit access to the bore. Possibly, the slot opening has a width and the bore has a width, and the width of the slot opening is less than the width of the bore. The bore may be circular in cross-section and the width of the bore may be the diameter of the bore.

Possibly, each support fixing comprises two channelling formations, which are arranged so that the slot openings face away from each other in opposite directions.

Possibly, the barrier member includes a barrier member fixing, also referred to as an intermediate fixing, which in an assembled condition may engage with one of the support fixings to fix the barrier member to the support. In moving from a disassembled condition to an assembled condition, each barrier member fixing may slidably engage with one of the support fixings.

Possibly, the barrier member fixing is releasably attachable to the respective barrier member piece.

Each barrier member fixing may comprise a bead formation or rod, which in the assembled condition locates in the bore, and may slidably locate in the bore. Possibly, the bead formation is circular in cross-section, and may be elongate, and may form an edge of the barrier member or barrier member piece. Possibly, the bead formation has a cross-section dimension which is greater than the slot width, so that the bead formation cannot easily pass through the slot opening in a lateral direction. Possibly, the bead cross-section dimension is a diameter of the bead formation.

Possibly, one or more of the barrier member pieces includes two spaced apart barrier member fixings which extend along two edges of the respective barrier member piece, which edges may be parallel and may face oppositely away from each other.

Possibly, the support includes two spaced apart support fixings, which may be parallel and may face towards each other.

Possibly, in moving to the assembled condition, the two barrier member fixings engage the two support fixings substantially simultaneously and slide therealong simultaneously.

Possibly, the support comprises a single module frame, which may comprise two single module frame side wall parts, two single module frame end wall parts and a single module frame roof part.

Possibly, the single module frame has an apex height, a side wall height, a width and a length.

Possibly, the single module frame width is greater than its apex height, which is greater than its length.

Possibly, the single module frame apex height is no more than 2.7 m, and desirably no more than 2.5 m, possibly no less than 2.1 m and desirably no less than 2.3 m.

Possibly, the single module frame side wall height is no more than 2.0 m, and desirably no more than 1.8 m, possibly no less than 1.4 m and desirably no less than 1.6 m.

Possibly, the single module frame width is no more than 3.3 m, and desirably no more than 3.1 m, possibly no less than 2.7 m and desirably no less than 2.9 m.

Possibly, the single module frame length is no more than 1.8 m, and desirably no more than 1.6 m, possibly no less than 1.2 m and desirably no less than 1.4 m.

Possibly, the barrier member pieces include a barrier member side wall piece, a barrier member end wall apex piece, a barrier member end wall lower piece and a barrier member roof piece. Possibly, the barrier member end wall lower piece is substantially the same as the barrier member side wall piece.

Possibly, the barrier member comprises a barrier member end wall, which comprises one of the barrier member end wall apex pieces and two of the barrier member end wall lower pieces. Possibly, each of the barrier member end wall apex pieces is fastened to two of the barrier member end wall lower pieces by a fastening e.g. a hook and fleece fastening.

Possibly, the structure comprises one single module frame, two barrier member side wall pieces, two barrier member end wall apex pieces, four barrier member end wall lower pieces and a barrier member roof piece.

Possibly, in the assembled condition, the roof piece is fastened at each end to one of the side wall pieces by a fastening, e.g. a hook and fleece fastening.

Possibly, the support includes one or more additional module frames, each of which may include two single module frame side wall parts, one single module frame end wall part and a single module frame roof part.

Possibly, each additional module frame has an apex height, a side wall height, a width and a length which may be substantially similar to those of the single module frame.

Possibly, the structure comprises a single module frame, one or more additional module frames, two barrier member wall pieces, two end wall apex pieces, four end wall lower pieces and a roof piece, with additionally, for each additional module frame, two of the barrier member side wall pieces and one of the barrier member roof pieces.

Possibly, the support and the barrier member together define the interior.

Possibly, the support members comprise one or more fixing support members. Possibly, the or each fixing support member comprises at least one of the support fixings, which may be formed integrally therewith.

Possibly, the support members comprise one or more plain support members, the or each of which do not comprise one of the support fixings.

Possibly the structure provides protection for the plant part, and may comprise a plant protection structure.

According to another aspect of the present disclosure, there is provided a method of controlling pollination of a plant, the method including providing a plant pollination control structure, the structure including a relatively rigid support and a relatively flexible barrier member, the barrier member being supported by the support, the barrier member defining an interior.

Possibly, the structure includes any of the features described in any of the preceding statements or following description. Possibly, the method includes any of the steps described in any of the preceding statements or following description.

FIGURES

Embodiments of the present disclosure will now be described, by way of example only, and with reference to the accompanying drawings, in which:

FIGS. 1A, 1B and 1C are perspective views of constituent pieces of a support of a plant pollination control structure in a disassembled or partially disassembled condition;

FIG. 2 is a perspective view of the support in an assembled condition;

FIG. 4 is a perspective view of a second plant pollination control structure;

FIGS. 5A and 5B are perspective views of the structure of FIG. 4, with FIG. 5A showing part of an interior and FIG. 5B showing a door opening;

FIG. 6 is a perspective view of a single module frame support and support fixings of a third plant pollination control structure, with the support fixings exploded away from the support;

FIG. 7 is a schematic plan view of the single module frame support of FIG. 6, with the support fixings attached to the support and barrier member pieces located alongside in a disassembled condition;

FIGS. 8A and 8B are schematic cross sections of the support fixings and barrier member fixings of the third plant pollination control structure in an assembled condition, with FIG. 8A showing an end wall location and FIG. 8B showing a side wall location;

FIG. 13A is a perspective view of a support member and a corner joint connector of a fourth plant pollination control structure in a disassembled condition and FIG. 13B is an end view on the support member of FIG. 13A;

FIG. 14A is a perspective view of a support of the fourth plant pollination control structure and FIG. 14B is a perspective view showing barrier member pieces being assembled to the support of FIG. 14A;

FIG. 15 is a perspective view of a support of a fifth plant pollination control structure;

FIG. 16 is a perspective view of a support of a sixth plant pollination control structure;

FIG. 17 is an end view of a support member and barrier member of a seventh plant pollination control structure in a disassembled condition;

FIG. 18 is a perspective view of the seventh plant pollination control structure in a partly assembled condition;

FIG. 19 is a relatively enlarged detail of part of the seventh plant pollination control structure taken from FIG. 18 as indicated by reference label XIX;

FIG. 20 is a perspective view of the seventh plant pollination control structure in an assembled condition;

Figure 3:
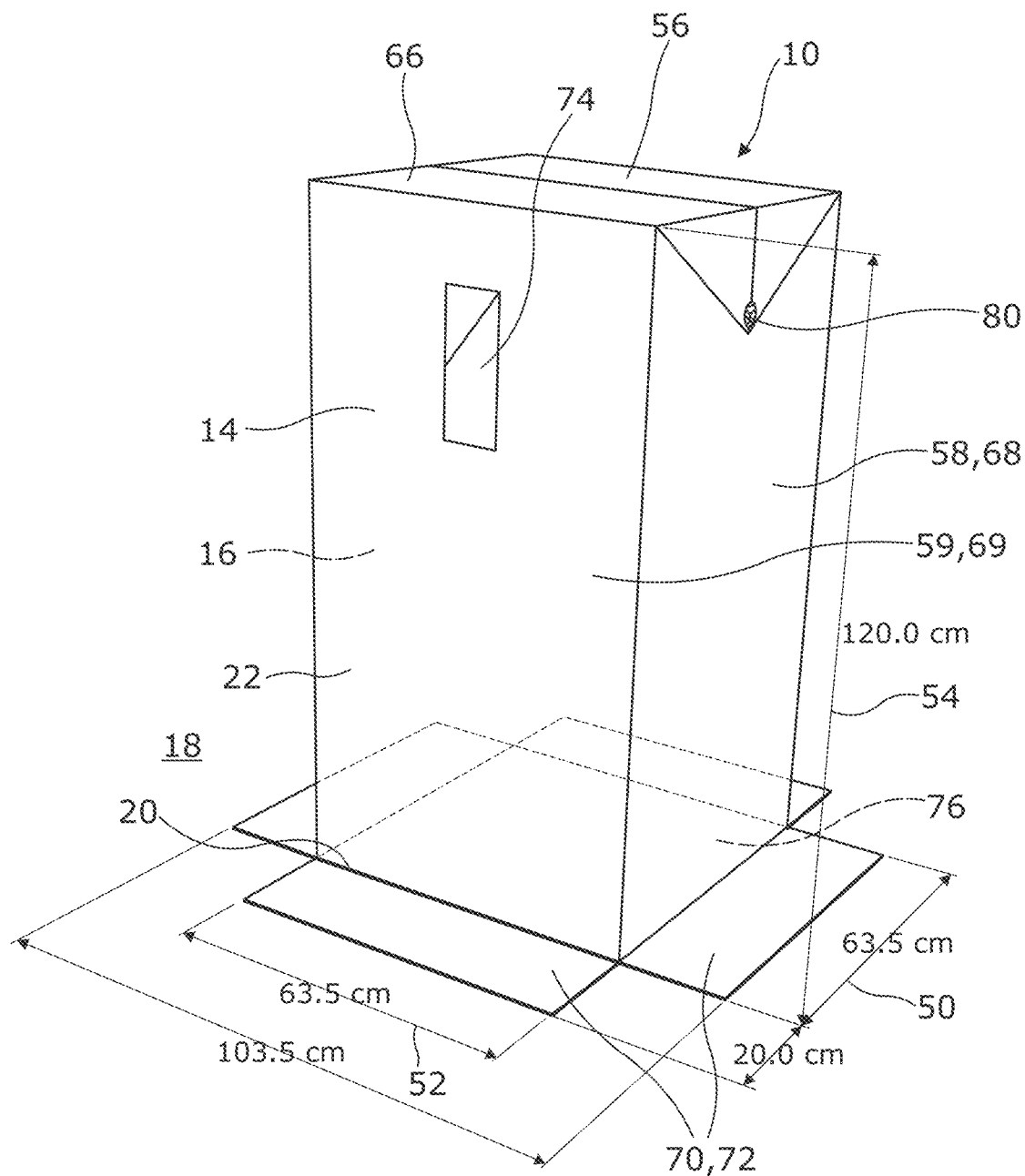
FIG. 3 is a perspective view of the plant pollination control structure in an assembled condition.

In the drawings, where multiple instances of the same or similar features exist, only a representative one or some of the instances of the features have been provided with numeric references for clarity.

In the drawings, where necessary, the general locations of features which are hidden (eg are behind or inside another feature) are indicated by numeric references with regular dashed leader lines.

DESCRIPTION

First Embodiment

FIGS. 1 to 3 show a plant pollination control structure 10, the structure 10 including a relatively rigid support or frame 12 and a relatively flexible barrier member or cover 14. The barrier member 14 is supported by the support 12. The barrier member 14 defines an interior 16. The support 12 is located in the interior 16.

In use, the support 12 is free standing, independent of the barrier member 14. The barrier member 14 is not free standing.

The barrier member 14 could include a window area 74 which is formed of transparent material to enable viewing of the interior 16.

The barrier member 14 comprises a material, which could be a textile material. The material could be translucent and could permit vapour transmission therethrough.

The material could be non-woven and could comprise a synthetic polymer, which could comprise one or more of polyester, polypropylene and/or polypropylene. The material could comprise a mesh.

The support 12 could be formed of a plastics material and could be formed by moulding.

The support 12 includes a plurality of elongate struts or support members 34, which are held together by connection arrangements 36. The connection arrangements 36 of this embodiment are arranged to permit assembly, disassembly and re-assembly of the support 12 without the use of tools. In one example, the support members 34 and the connection arrangements 36 are held together by push fit action.

The connection arrangements 36 comprise female connectors 42, which comprise a plurality of socket recesses 38 and, in this embodiment, comprise female corner joint connectors 42A each of which defines three socket recesses 38, which are angled at 90° relative to each other.

Each support member 34 includes one or more projecting parts 40, each of which comprises an end 44 of the support member 34 and which, in the assembled condition, is received in one of the socket recesses 38 of one of the corner joint connectors 42A.

The connection arrangements 36 comprise a male straight connector 46, which connects two of the support members 34 together in line. The straight connector 46 comprises a body 48 and two projecting parts 40 which extend in opposite directions from the body 48.

Each support member 34 defines one socket recess 38 at each end 44, in which, in use, one of the straight connector projecting parts 40 is receivable in the assembled condition.

Each support member 34 is tubular and hollow, in the form of a pipe.

The support members 34 are circular in cross-section. The connection arrangements 36 are rounded.

The structure 10 has a length 50, a width 52 and a height 54.

In this embodiment, the structure height 54 is greater than its width 52 and its length 50. The width 52 and the length 50 are substantially the same.

The structure 10 has a plurality of horizontal cross-sectional interior areas at different distances up its height 54. In this embodiment, the horizontal cross-sectional areas are substantially the same at all of the distances up the height 54.

The structure 10 comprises a roof 56, two side walls 58 and two end walls 59. The structure 10 does not comprise a floor.

The roof 56 is substantially planar, and in the installed condition is substantially horizontal. All of the side walls 58 and the end walls 59 are substantially the same size, are substantially planar and in the installed condition extend substantially vertically.

The support 12 comprises a base part 60, side wall parts 62, end wall parts 63 and a roof part 64. Each of the base part 60, the side and end wall parts 62, 63 and the roof parts 64 is substantially planar. The base part 60 and the roof part 64 each comprise four corner joint connectors 42A with four equal lengths of support members 34 extending therebetween. The side and end wall parts 62, 63 comprise four equal lengths of support members 34 extending between the corner joint connectors 42A of the base part 60 and the roof part 64. In this embodiment, all of the support members 34 are straight.

The barrier member 14 comprises a roof part 66 and side and end wall parts 68, 69, which locate against or alongside, respectively, the support roof part 64 and the support side and the end wall parts 58, 59.

The barrier member 14 includes securing features 70 to secure the structure 10 to the ground surface 18 in the installed condition. The securing features 70 could comprise skirt extensions 72, which could extend outwardly from a lower edge of each of the barrier member side and end wall parts 68, 69, at the level of the support base part 60. The skirt extensions 72 could be formed of the same material as the barrier member 14, and could be formed integrally as part of the barrier member 14.

In some embodiments the skirt extensions 72 and the barrier member 14 are formed of different materials from each other. For example, in one example the barrier member 14 may be formed of non-woven fabric material and the skirt extensions 72 may be formed of a tougher, more durable material than the barrier member 14, for example a plastics material such as PVC.

One of the barrier member side or end wall parts 68, 69 defines a window area 74, which is formed of transparent material to enable viewing of the interior 16.

The barrier member 14 is formed to a shape to fit over the support 12. In one example, the barrier member 14 is pre-formed to the shape. In this embodiment the pre-formed shape is in the form of a cuboid.

In a pre-assembly condition, the barrier member 14 could be formed of flat sheet material, which is formed into a bag, which has a single upper edge with two upper corners and two lower open edges which define an opening.

In the installed condition, the bag is folded and each of the two upper corners is fastened by a fastening 80 (e.g., adhesive, a weld, a rivet or similar) to a different one of the barrier member side or end wall parts 68, 69.

The structure 10 defines a floor opening 76, through which, in use in moving to the installed condition, the plant or plant part passes to locate in the interior 16 in the installed condition.

In other examples, the barrier member 14 could be formed to the shape to fit over the support 12 in situ.

In this embodiment, the barrier member 14 is provided as a single piece and is formed from a single piece of material.

In one example, in the assembled condition, the structure height 54 is no more than 1.5 m, and desirably no more than 1.3 m, no less than 0.9 m and desirably no less than 1.1 m. In one example, the structure height is 1.2 m.

In one example, in the assembled condition, the structure width 52 and the structure length 50 are no more than 1.5 m, and desirably no more than 1.0 m, possibly no less than 0.5 m and desirably no less than 0.75 m.

The barrier member 14 is not fixed to the support 12, but is held in position by virtue of the shape and the fit to the support 12 and, in the installed condition, by the securing features 70.

In Use

In use, in moving to the installed condition, the support 12 is firstly located over the plant and then the barrier member 14 is located on the support 12, over the plant. The support 12 is located on the ground surface 18 and could be anchored thereto by, for example, pegs (not shown). The barrier member 14 contacts the ground surface 18 in a substantially continuous contact line 20 around the interior 16. The barrier member 14 and the ground surface 18 together form a substantially continuous enclosure 22 around the interior 16.

The plant could be rooted in a ground surface material. Thus, in the installed condition, a part of the plant could be located in the interior 16, and another part of the plant could be located in the ground surface 18.

For stability, weighting means which may take the form of a weight or weights could be located on the skirt extensions 72 to seal and secure or anchor the structure 10 to the ground surface 18.

The skirt extensions 72 and weights are especially useful when the structure 10 is located or assembled on an uneven ground surface. In this case, there may exist significant gaps between the base of the structure 10 and the surface of the ground, and the skirt extensions 72, in combination with the weights, guard against uncontrolled movement of pollen through these gaps.

The weight or weights hold down the skirt extensions 72 to provide an additional anchor for the structure and to prevent the skirt extensions from being blown up by gusts of wind, for example.

In some embodiments, the weight or weights may be water bags and/or sand bags. In some embodiments, the weight or weights may take the form of soil placed or piled on top of the skirt extensions 72. In some embodiments, the weight or weights may be integral with or provided within the skirt extensions 72, or may be provided within pockets of the skirt extensions.

Other Embodiments

FIGS. 4 to 20 show other embodiments of the disclosure, many features of which are similar to those already described in relation to the embodiment of FIGS. 1 to 3. Therefore, for the sake of brevity, the following embodiments will only be described in so far as they differ from the embodiment already described. Where features are the same or similar, the same reference numerals have been used and the features will not be described again.

Second Embodiment

FIGS. 4, 5A and 5B show a second embodiment of the disclosure, a plant pollination control structure 210.

The structure 210 includes a pair of side walls 58, a pair of end walls 59 and a roof 56. The structure roof 56 includes an apex line 78, which is aligned parallel to the structure length 50.

The structure roof 56 is curved convexly from the top of the side walls 58 to the apex line 78. The end walls 59 extend upwardly to the apex line 78.

In the example shown, one of the end walls 59 defines the window area 74.

In the example shown, one of the end walls 59 also defines an opening 28 in the form of a door opening 75 as will now be described. As shown in FIG. 5B, one of the end walls 59 comprises an opening wall 82 which is arranged to provide a person access opening 84 to permit access for a person to the interior 16. The opening wall 82 includes a pair of parts 82A, 82B which are movable between a closed condition and an open condition to provide the person access opening 84. The opening wall 82 includes a securing arrangement 86 to secure the opening wall parts 82A, 82B in the closed condition. In the example shown, the securing arrangement 86 comprises a releasable fastening 88 (e.g., complementary strips of hook and loop material), which extends substantially a greater portion of, or the whole, height of the respective barrier member end wall 59, and could extend substantially the whole height of the structure 210.

Referring to FIG. 5A, the roof support part 64 includes curved roof support members 90 and a plurality of lines of straight support members 92.

In some embodiments, the curved roof support members 90 have a degree of flexibility that allows them to move with respect to the rest of the support. This is useful during strong winds, for example, as it reduces the pressure on the barrier member, which would otherwise be the only relatively flexible and movable member of the structure. The curvature of the roof, combined with its flexibility, is advantageous also because it helps to direct the wind up and over the structure, again taking pressure off of the barrier member material. Thus, the likelihood of the barrier member tearing or damaging in high winds, for example, is reduced. This is especially useful in embodiments in which the barrier member, or at least part of the barrier member, is formed of relatively fragile non-woven material.

In one example, flexibility of the curved roof support members 90 is achieved by providing the roof support members 90 as hollow plastic pipes. In some cases the hollow plastic pipes are made of medium-density polyethylene (MDPE).

The straight support members 92 comprise cross members 94 which extend across the interior 16; apex support members 96 which substantially extend along the apex line 78; and roof bracing members 152 which extend from the cross members 94 upwardly to the apex support members 96.

The straight support members 92 are provided in a module length, which could be 1500 mm, and which length determines the structure width 52, length 50 and height 54. The length 50 could comprise more than one module length.

The connection arrangement 36 could include female connectors 42, which could comprise corner joint connectors 42A, straight connectors 42B and tee connectors 42C and curved connectors 42D. The support members 90, 92 could locate within the socket recesses 38 of the connectors 42. Each connector 42 could include a locking arrangement (not shown) such as a grub screw located through a threaded hole in the connector 42 and tightened against the respective support member 90, 92 to lock the support member 90, 92 in the assembled condition.

The structure 210 has an apex height 160, a side wall height 162, a width 52 and a length 50. In this embodiment, the structure length 50 is greater than the apex height 160, which is greater than the width 52, which is substantially the same as the side wall height 162.

The horizontal cross-sectional areas are substantially the same at all of the distances up the height 54, up to the top of the side walls 58 and then the horizontal cross-sectional areas decrease up to the apex line 78.

In one example, the structure length 50 is no more than 3.3 m, and desirably no more than 3.1 m, no less than 2.7 m and desirably no less than 2.9 m. In one example, the structure length 50 could be 3.0 m.

In one example, the apex height 160 is no more than 2.3 m, and desirably no more than 2.1 m, no less than 1.7 m and desirably no less than 1.9 m. In one example, the apex height 160 could be 3.0 m.

In one example, the width 52 and the side wall height 162 could be no more than 1.8 m, and desirably no more than 1.6 m, no less than 1.2 m and desirably no less than 1.4 m. In one example, the width 52 and the side wall height 162 could be 1.5 m.

Advantageously, the plant pollination control structure 210 permits a person to enter and work within the interior 16.

Third Embodiment

FIGS. 6 to 12 show a third embodiment of the disclosure, a plant pollination control structure 310.

The structure 310 includes a barrier member fixing arrangement 98 to fix the barrier member 14 to the support 12. The barrier member 14 comprises a plurality of barrier member pieces 110, which are separate from each other, and each of which is fixed, separately, to the support 12.

The barrier member fixing arrangement 98 includes a support fixing 112, which, in the assembled condition, is fastened to the support 12 by fasteners (not shown) such as bolts or screws. Each support fixing 112 is elongate and comprises two elongate channelling formations 114, each of which extends the full length of the respective support fixing 112.

Each channelling formation 114 defines a channel 116 which extends along the full length of the channelling formation 114. Each channel 116 comprises a bore 118 which extends along the length of the channel 116 and a slot opening 120 which also extends along the length of the channel 116 and extends laterally outwardly to permit access to the bore 118. The slot opening 120 has a width and the bore 118 has a width, and the width of the slot opening 120 is less than the width of the bore 118. The bore 118 is substantially circular in cross-section and the width of the bore 118 is the diameter of the bore 118.

The two channelling formations 114 are arranged so that the slot openings 120 face away from each other in opposite directions.

Each of the barrier member pieces 110 includes a barrier member fixing 122, which in the assembled condition engages with one of the support fixings 112 to fix the barrier member piece 110 to the support 12. The barrier member fixings 122 comprise the barrier member fixing arrangement 98. In moving from a disassembled condition to the assembled condition, each barrier member fixing 122 slidably engages with one of the support fixings 112.

Figure 9:
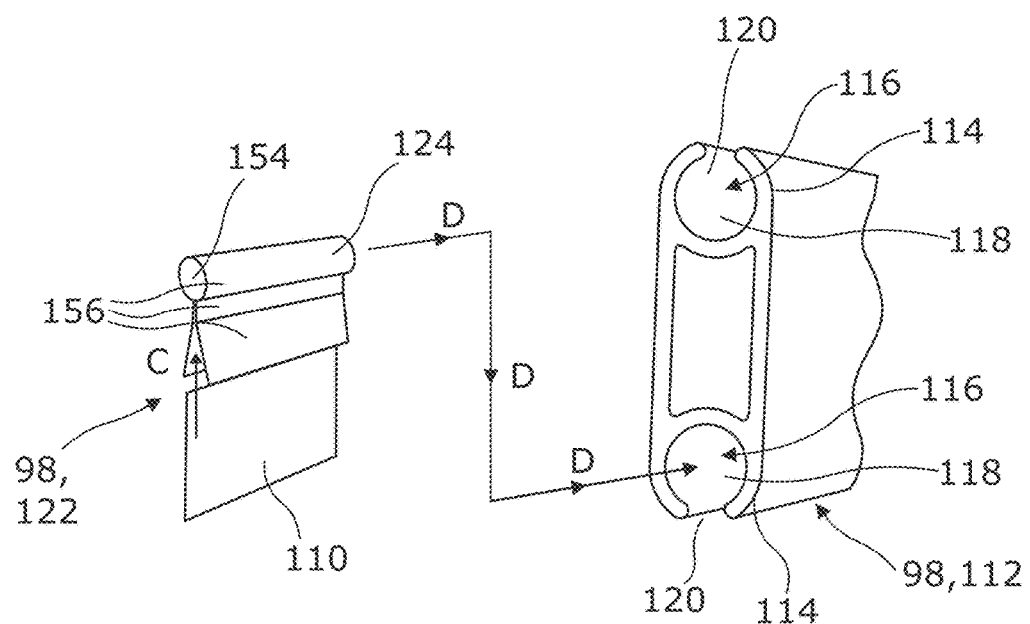
FIG. 9 is a schematic perspective view of an edge part of a barrier member of the third plant pollination control structure with part of a barrier member fixing in a disassembled condition, along with an end of one of the support fixings (NB the parts are shown at different scales)

Each barrier member fixing 122 comprises an elongate bead formation 124, which, in the assembled condition, slidably locates in the bore 118 (as indicated by arrows D in FIG. 9). The bead formation 124 is substantially circular in cross-section, and forms an edge of the respective barrier member piece 110. The bead formation 124 has a cross-section dimension (in this case, a diameter) which is greater than the width of the slot opening 120, so that the bead formation 124 cannot easily pass through the slot opening 120 in a lateral direction.

Referring to FIG. 9, the bead formation 124 comprises a core 154 and an attachment material 156 which extends from one surface of the barrier member piece 110, around the core 154 to an opposite surface of the barrier member piece 110. An edge part of the barrier member piece 110 is thus received between two layers of the attachment material 156 (as indicated by arrow C in FIG. 9) and is affixed therebetween e.g., by stitching, bonding or any other suitable means so that the bead formation 124 forms an edge of the barrier member piece 110.

One or more of the barrier member pieces 110 includes a pair of parallel spaced apart barrier member fixings 122 which extend along two parallel edges of the respective barrier member piece 110, which edges face oppositely away from each other.

The support 12 includes one or more pairs of parallel, spaced apart, support fixings 112. In moving to the assembled condition, the two barrier member fixings 122 engage the two support fixings 112 substantially simultaneously and slide therealong simultaneously.

As shown in FIG. 6, the support 12 comprises a single module frame 126, which comprises two single module frame side wall parts 128, two single module frame end wall parts 130 and a single module frame roof part 132. Each of the parts 128, 130 132 comprises support members 34. The support members 34 could be assembled together to form the parts 128, 130, 132 in a way which permits disassembly, for example by screwing, bolting or using brackets or permanently eg by welding.

In one example, the support members 34 are formed of hollow section steel.

The parts 128, 130, 132 are desirably assembled together to form the single module frame 126 in a way which permits disassembly, for example by screwing, bolting or using brackets.

The support fixings 112 are fastened to some faces of the some of the support members 34 as shown by arrows F in FIG. 6, for example, by bolting or screwing.

The single module frame 126 has an apex height 144, a side wall height 150, a width 146 and a length 148.

The single module frame width 146 is greater than its apex height 144, which is greater than its length 148.

In one example, the single module frame apex height 144 could be no more than 2.7 m, desirably no more than 2.5 m, no less than 2.1 m and desirably no less than 2.3 m. In one example, the single module frame apex height 144 could be 2.4 m.

In one example, the single module frame side wall height 150 could be no more than 2.0 m, desirably no more than 1.8 m, no less than 1.4 m and desirably no less than 1.6 m. In one example, the single module frame side wall height 150 could be 1.7 m.

In one example, the single module frame width 146 could be no more than 3.3 m, desirably no more than 3.1 m, no less than 2.7 m and desirably no less than 2.9 m. In one example, the single module frame width 146 could be 3.0 m.

In one example, the single module frame length 148 could be no more than 1.8 m, desirably no more than 1.6 m, no less than 1.2 m and desirably no less than 1.4 m. In one example, the single module frame length 148 could 1.5 m.

Figure 10:
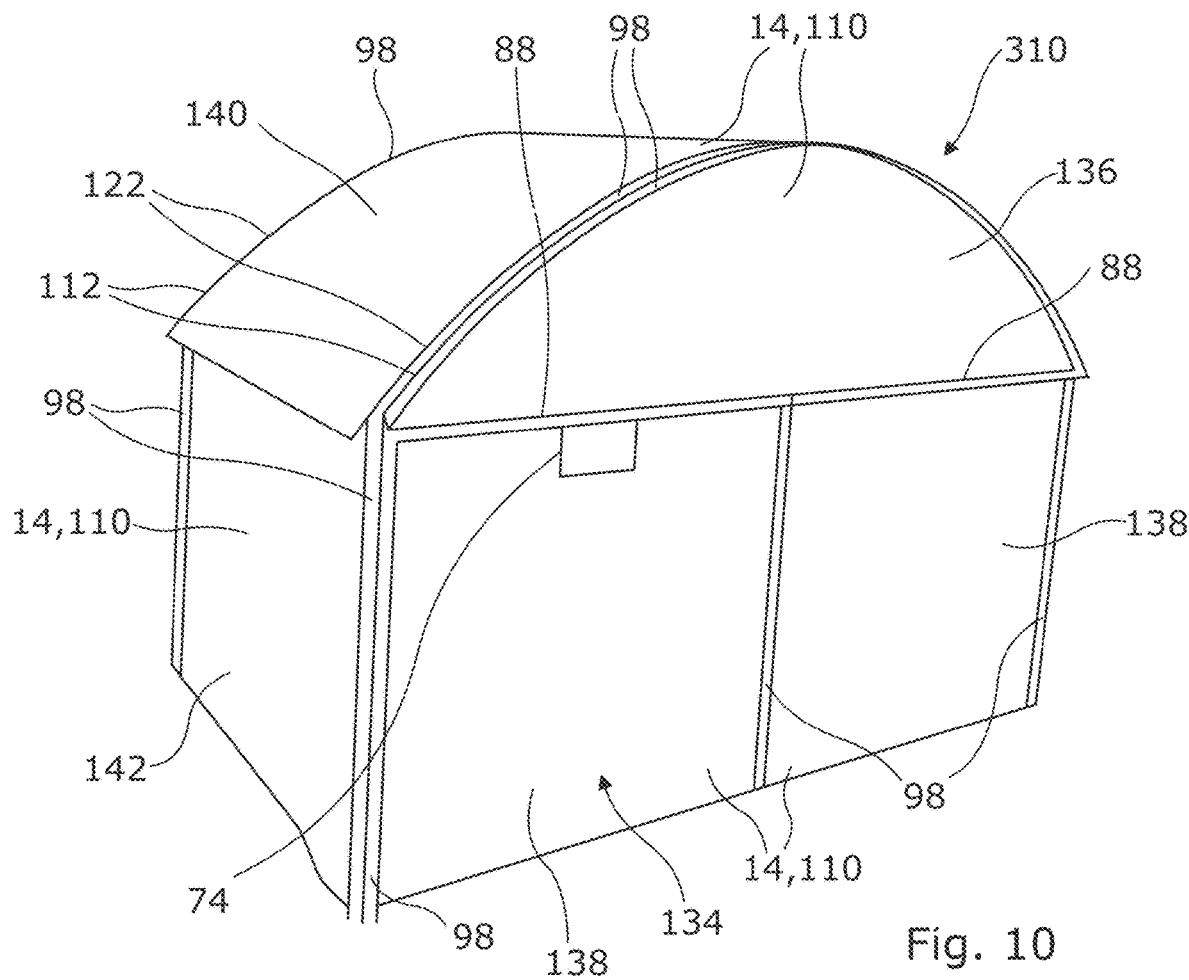
FIG. 10 is a perspective view of the third plant pollination control structure comprising the single module frame support, in an assembled condition.

Referring to FIGS. 7 and 10, the barrier member pieces 110 include a barrier member side wall piece 142, a barrier member end wall apex piece 136, a barrier member end wall lower piece 138 and a barrier member roof piece 140. The barrier member end wall lower piece 138 is substantially the same as the barrier member side wall piece 142.

The barrier member 14 comprises a barrier member end wall 134, which comprises one of the barrier member end wall apex pieces 136 and two of the barrier member end wall lower pieces 138. Each of the barrier member end wall apex pieces 136 is fastened to two of the barrier member end wall lower pieces 138 by a fastening 88 e.g., a hook and fleece fastening.

In the example shown in FIG. 10, the structure 310 comprises one single module frame 126, two barrier member side wall pieces 142, two barrier member end wall apex pieces 136, four barrier member end wall lower pieces 138 and a barrier member roof piece 140.

The structure 310 is assembled as follows. The single module frame 126 is firstly constructed in situ. The barrier member pieces 110 are then separately attached to the single module frame 126. It will be noticed that, except on the apex end wall, the support fixings 112 are arranged in pairs and the barrier member fixings 122 are arranged in corresponding pairs. Thus, each of the barrier member roof piece 140, the barrier member end wall lower pieces 138 and the barrier member side wall pieces 142 includes a pair of the barrier member fixings 122 located on two parallel edges, which edges face oppositely away from each other.

Taking as an example the barrier member roof piece 140, the two ends of the barrier member fixings 122 of the barrier member roof piece 140 are located in the corresponding support fixings 112 located on the curved roof members 90 and are slid therealong as indicated by arrow A in FIG. 6, until the barrier member fixings 122 of the barrier member roof piece 140 extend substantially wholly along the support fixings 112 of the curved roof members 90 and the barrier member roof piece 140 covers the curved roof members 90. The barrier member end wall lower pieces 138 and the barrier member side wall pieces 142 are assembled to the single module frame 126 in a similar way, as shown schematically in cross-section plan in FIGS. 7, 8A and 8B.

The barrier member end wall apex piece 136 includes a barrier member fixing 122 along its curved edge which is located in the support fixing 112 of the one of the curved roof members 90. With the barrier member end wall apex piece 136 and the barrier member end wall lower pieces 138 assembled to the single module frame 126, the barrier member end wall apex piece 136 and the barrier member end wall lower pieces 138 are then fastened together by the fastening 88.

In the assembled condition, the roof piece 140 is fastened at each end to one of the side wall pieces 142 by another fastening 88 e.g., a hook and fleece fastening.

A particular advantage of the third plant pollination control structure 310 is that the barrier member 14 is fixed to the support 14 (rather than being a loose cover as in the embodiments of FIGS. 1 to 5). This prevents or reduces abrasion of the barrier member 14 as the structure 310 moves (for example in wind). This means that a thinner, more fragile material (such as non-woven material formed of synthetic polymers such as polyester or polypropylene) can be used for the barrier member 14 than would otherwise be the case. This allows the material of the barrier member 14 to be chosen based, to a greater extent, on its pollination control properties rather than its strength. Also, if part of the barrier member 14 is damaged, only the piece(s) 110 which are damaged need be replaced.

The support 12 could include one or more additional module frames 158. Each additional module frame 158 has an apex height, a side wall height, a width and a length which are substantially similar to those of the single module frame 126.

Figure 11:
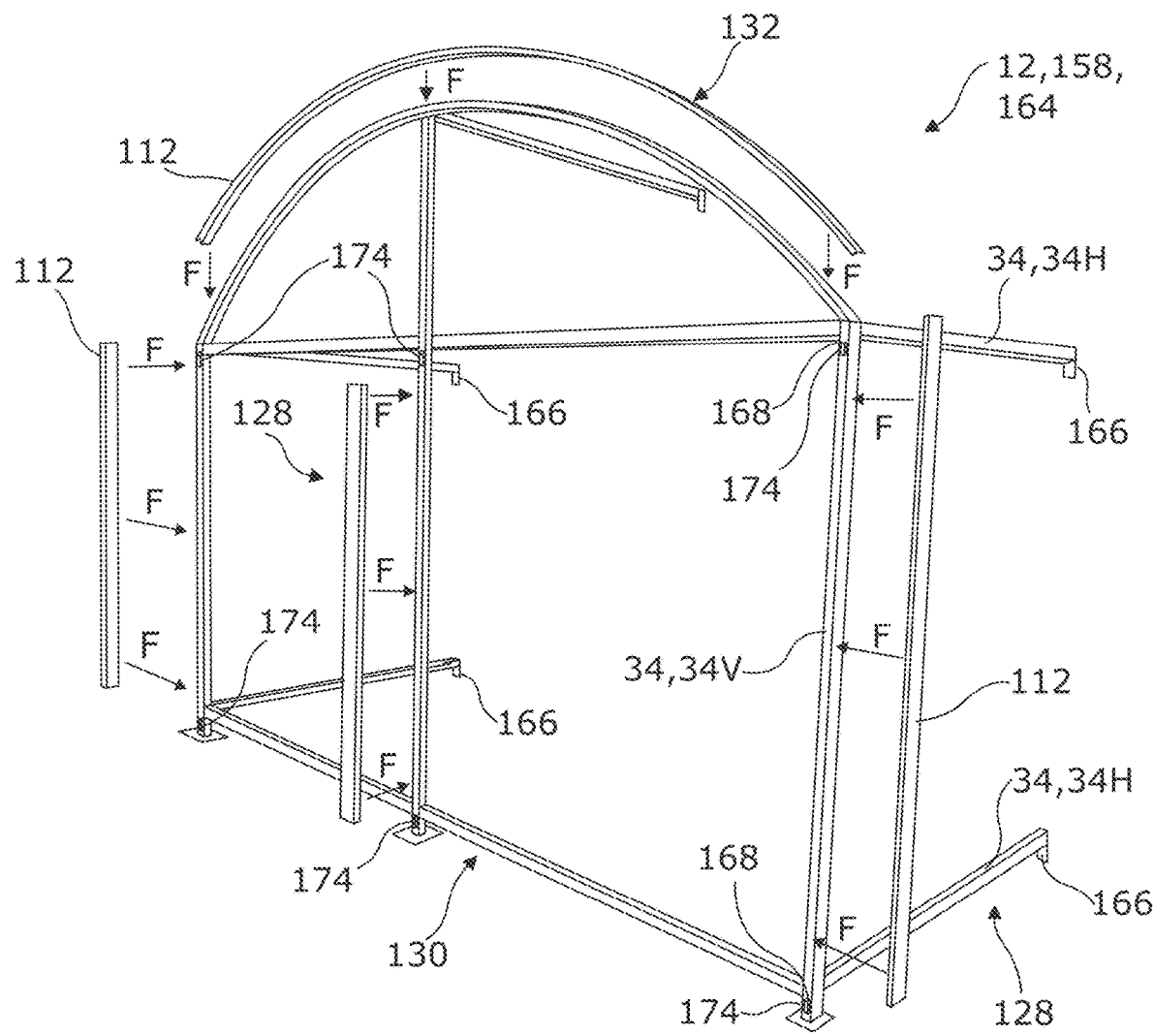
FIG. 11 is a perspective view of an additional module frame support and support fixings of the third plant pollination control structure, with the support fixings exploded away from the support.

The additional module frames 158 could include an additional end module frame 164, one example of which is shown in FIG. 11. Each additional end module frame 164 includes two single module frame side wall parts 128, one single module frame end wall part 130 and a single module frame roof part 132.

The support fixings 112 are fastened to some faces of the some of the support members 34 of the additional end module frame 164 as shown by arrows F in FIG. 11.

FIG. 11 also shows an example of how the module frames 126, 158, 164 could be constructed. Each of the frames 126, 158, 164 comprises horizontal support members 34H and vertical support members 34V. The horizontal support members 34H include tabs 166, one of which extends downwardly from each end. Each of the vertical support members 34V includes loop members 174 which define tab receiving recesses 168. In the assembled condition, the tabs 166 locate in the tab receiving recesses 168.

In use, additional end module frames 164 can be added end to end to the single module frame 126 as required to extend its length. The structure 310 could then comprise one single module frame 126, and one or more additional end module frames 164, two barrier member side wall pieces 142, two end wall apex pieces 136, four end wall lower pieces 138 and a roof piece 140, with additionally, for each additional end module frame 164, two of the barrier member side wall pieces 142 and one of the barrier member roof pieces 140.

The support 12 could include a plurality of the single module frames 126 which are located side by side to extend the width of the structure 310.

Alternatively, the support 12 could include a single module frame 126, a plurality of additional end module frames 164 to extend the length of the structure 310, a plurality of additional side module frames 170 which add support members 34 to the single module frame to extend the width of the structure 310 and a plurality of additional side-end module frames 172 which extend both the width and the length of the structure 310.

Thus the additional module frames 158 could include additional end module frames 164; additional side module frames 170; and/or additional side-end module frames 172.

In another example, the support 12 could comprise a plurality of single module frames 126 which could be located alongside each other both length-wise and width-wise as required. The barrier member 14 of one single module frame 126 could be arranged to be fixed to the support fixing 112 of the adjacent single module frame 126 to provide a complete enclosure 22 with no gaps.

Figure 12:
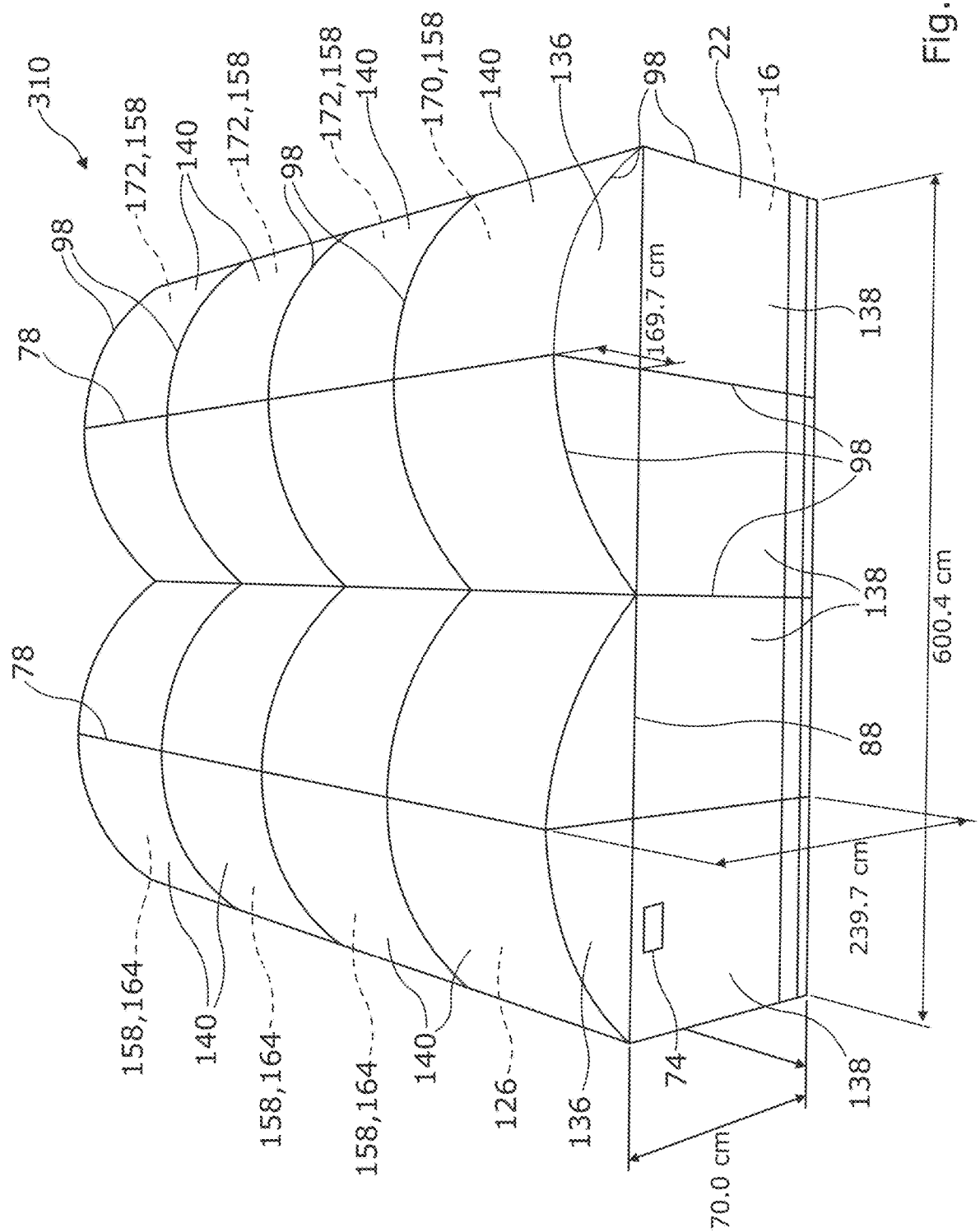
FIG. 12 is a perspective view of the third plant pollination control structure comprising a plurality of the single module frame supports and a plurality of the additional module frame supports.

FIG. 12 shows a structure 310 comprising (the locations of the frames being indicated generally by dashed leader lines in FIG. 12): one single module frame 126; three additional end module frames 164; one additional side module frame 170; and three additional side-end module frames 172.

The structure 310 then includes barrier member pieces 110 which are assembled to the module frames 126, 164, 170, 172 to provide a continuous barrier member 14 which, with the ground surface 18, provides an enclosure 22 around the interior 16.

The applicant has found that various sizes of structures 310 can be thus be formed from combinations of the single module frame 126, the additional module frames 158 and the barrier member pieces 110.

Fourth Embodiment

FIGS. 13 and 14 show a fourth embodiment of the disclosure, a plant pollination control structure 410.

In this embodiment, the support members 34 comprise fixing support members 34B. Each fixing support member 34B comprises at least one of the support fixings 112 of the third embodiment and is formed integrally therewith.

In the example shown, the fixing support members 34B are of similar size circular cross-section to the support members 34 of the first embodiment 10 shown in FIGS. 1 and 2 and can utilise the same or similar corner joint connectors 42A.

Each fixing support member 34B comprises two elongate channelling formations 114, each of which extends the full length of the respective fixing support member 34B.

As in the third embodiment shown in FIG. 9, each channelling formation 114 defines a channel 116 which extends along the full length of the channelling formation 114. Each channel 116 comprises a bore 118 which extends along the length of the channel 116 and a slot opening 120 which also extends along the length of the channel 116 and extends laterally outwardly to permit access to the bore 118. The slot opening 120 has a width and the bore 118 has a width, and the width of the slot opening 120 is less than the width of the bore 118. The bore 118 is substantially circular in cross-section and the width of the bore 118 is the diameter of the bore 118.

The two channelling formations 114 of each fixing support member 34B are arranged so that the slot openings 120 face away from each other in opposite directions.

FIG. 14A shows a support 12 of the fourth plant pollination control structure 410 comprising support members 34, which comprise plain support members 34A of plain circular cross-section (which do not comprise one of the support fixings 112) and fixing support members 34B.

The fixing support members 34B are arranged in pairs, comprising two pairs of vertically extending fixing support members 34BV and a pair of horizontally extending fixing support members 34BH.

FIG. 14B shows barrier member pieces 110 being fitted to the support 12. In the example shown, the barrier member pieces 110 comprise a roof and side walls piece 178 and two end wall pieces 134A. Each of the barrier member pieces 110 includes a pair of spaced apart barrier member fixings 122 which extend along two parallel edges of the respective barrier member piece 110, which edges face oppositely away from each other.

In moving to the assembled condition, the barrier member fixings 122 of the roof and side walls piece 178 are slid up and along the corresponding channels 116 of one pair of the vertically extending fixing support members 34BV, across and along the channels 116 of the horizontally extending fixing support members 34BH and down and along the channels 116 of the other pair of the vertically extending fixing support members 34BV as indicated by arrows J. Thus, in this embodiment, the roof and side walls piece 178 provides two side walls and a roof as a single continuous piece.

Similarly, the barrier member fixings 122 of each end wall piece 134A are slid up and along corresponding channels 116 of the vertically extending fixing support members 34BV as indicated by arrows K to form end walls of the structure 410. The top edges of the end wall pieces 134A could be fastened to the roof and side walls piece 178 by a fastening 88 e.g., a hook and fleece fastening.

Advantageously, this embodiment combines the advantages of the first and second embodiments, namely, simple, economic, lightweight construction, easy build, quick assembly and disassembly, with the advantages of the third embodiment, namely fixing of the barrier member to the support to reduce barrier member damage. The arrangement of this embodiment has been found to be particularly suitable for smaller structures such as those having a floor area of less than 3 m by 1.5 m and more desirably of 1.5 m by 1.5 m.

Fifth and Sixth Embodiments

FIGS. 15 and 16 show fifth and sixth embodiments of the disclosure, plant pollination control structures 510, 610. In each case, the support 12 is similar to that of the fourth embodiment, but the support members 34B include, respectively, angled roof members 176 and curved roof members 90.

Seventh Embodiment

FIGS. 17 to 20 show a seventh embodiment of the disclosures, a plant pollination control structure 710.

In this embodiment, the support 12 comprises fixing support members 34B similar to those described above for the fourth embodiment 410, in which each fixing support member 34B comprises two elongate channelling formations 114 each defining a channel 116. The barrier member 14 comprises a plurality of panels or pieces 110, each of which includes a bead formation 124, which, in the assembled condition, locates in one of the channels 116.

However, in this embodiment, referring to FIG. 17, the attachment material 156 of the bead formations 124 of the barrier member fixings 122 comprises a releasable fastening 88 comprising a first area of hook or loop material 88A, which is located on one side of the attachment material 156.

Each of the barrier member pieces 110 includes a complementary second area of hook or loop material 88B in the form of a strip extending along one or more edge regions 180 on one side of the barrier member pieces 110. In this way, the barrier member fixings 122 act as intermediate fixings that can be releasably or removably attached or fixed to both the barrier member and the support. Specifically, the barrier member fixings 122 releasably attach to barrier member pieces 110 via the releasable fastenings 88, and releasably attach to the support 12 via the bead formation 124 which slidably locates in a channel 116 of a fixing support member 34B.

In one example, the fixing support members 34B are formed of metal, e.g., aluminium, by extrusion. The support 12 includes female connectors 42 which are formed of metal, for example, aluminium, by casting.

In assembling the seventh control structure 710, the bead formations 124 are firstly located in the bores 118 of the channels 116 of the fixing support members 34B. The fixing support members 34B are then located into the socket recesses 38 of the connectors 42 to form the support 12 as shown in FIGS. 18 and 19. When assembled in this way, the attachment material 156 of the barrier member fixings 122 extends into the openings defined between the fixing support members 34B. In the example shown, the support 18 also includes a pair of roof support members 90.

The barrier member pieces 110 are then assembled to the support 12 by simply fastening the second areas of hook or loop material 88B of the barrier member pieces 110 to the first areas of hook or loop material 88A to form the assembled structure 710 as shown in FIG. 20. The releasable fastenings 88 defined by the first and second areas of hook or loop material 88A, 88B are positioned adjacent the fixing support members 34B, within the openings defined between the fixing support members 34B that the barrier member pieces 110 cover in use. In this way, the barrier member pieces 110 are suspended within these openings, and do not overlie, overlap or otherwise contact the support 12. This is advantageous, because it prevents abrasion of the barrier member pieces 110 due to general contact with the support 12 in use, and in particular due to contact caused by the barrier member pieces 110 being blown against the support 12 during windy weather conditions. Avoiding this contact between the barrier member pieces 110 and the support 12 enables the barrier member pieces 110 to be formed from a more fragile material, such as a non-woven material, which may have better pollination control properties in certain scenarios. In that case, the attachment material 156 may be formed of a stronger, more durable material that is better able to withstand abrasion caused by contact with the support 12.

In the assembled condition as shown in FIG. 20, the edge regions 180 of the barrier member pieces 110 with the second areas of hook or loop material 88B are located on the inside of the barrier member pieces 110. In FIG. 20, the locations of the edge regions 180 are shown delineated on the outside surface of the barrier member pieces 110 and indicated by reference numerals 180, but in reality the delineation might only comprise lines of stitching and the edge regions 180 per se would not be visible from the outside. As shown, the edge regions 180 of the barrier member pieces 110 are offset from the fixing support members 34B of the support 12, so as to be positioned within the openings defined between the fixing support members 34B.

As shown in FIG. 20, the barrier member pieces 110 include two side wall pieces 142, two end wall pieces 134A and a roof piece 140.

Some of the barrier member pieces 110 have additional first areas of hook or loop material 88A (not shown) which in the assembled condition are located on the outside of the respective barrier member piece 110 and allow fastening of the second area of hook or loop material 88B of an adjacent barrier member piece 110 thereto eg, the roof piece 140 to the end wall piece 134A.

The side wall pieces 142 include flaps 182 extending from the upper corners thereof which fold around the support 12 and are fastened to the neighbouring roof piece 140, again, by complementary areas of hook and loop material, to cover over gaps between the barrier member pieces 110 at the upper corners of the support 12.

Advantageously, the structure 710 is strong but easily assembled and disassembled. Access to the interior 16 can be easily obtained by simply unfastening parts of the areas of the hook or loop materials 88. Barrier member pieces 110 can advantageously be detached from/attached to the structure 710 without disassembling the support 12 or adjusting or altering the engagement between the support 12 and the barrier member fixings 122. In this way, the support 12 can remain assembled whilst barrier member pieces 110 are detached and repaired and/or replaced.

Individual barrier member pieces 110 can be easily and quickly detached/attached independently of other barrier member pieces 110, this being especially useful when different parts of the barrier member are formed of different materials which may require replacement at different intervals, and/or when the barrier member is formed of a more fragile material which may require more frequent repair or replacement.

This structure 710 has been found particularly suitable for floor areas of 2.25 square metres (1.5 m by 1.5 m) up to 4.5 square metres (1.5 by 3 m).

The support 12 of the structure 710 shown in FIGS. 17 to 20 could comprise a single module frame 126 which can be used to construct a larger structure in a similar way to that described for the embodiment shown in FIG. 12.

Although not shown in FIG. 20, the structure 710 could include skirt extensions 72 extending from lower edges of the barrier member side and end wall pieces 142, 134A to seal and secure the structure 710 to the ground.

The skirt extensions 72 could be formed from nonwoven/mesh material (per the rest of the structure) or a plastic film (eg reinforced vinyl) which is easier to clean.

Other Modifications

Various other modifications could be made without departing from the scope of the disclosure. The structure, the support and the barrier member could be of any suitable size and shape, and could be formed of any suitable material (within the scope of the specific definitions herein).

The various components including the support members and the barrier member pieces could be of any suitable size and formed of any suitable material (within the scope of the specific definitions herein).

Figure 21:
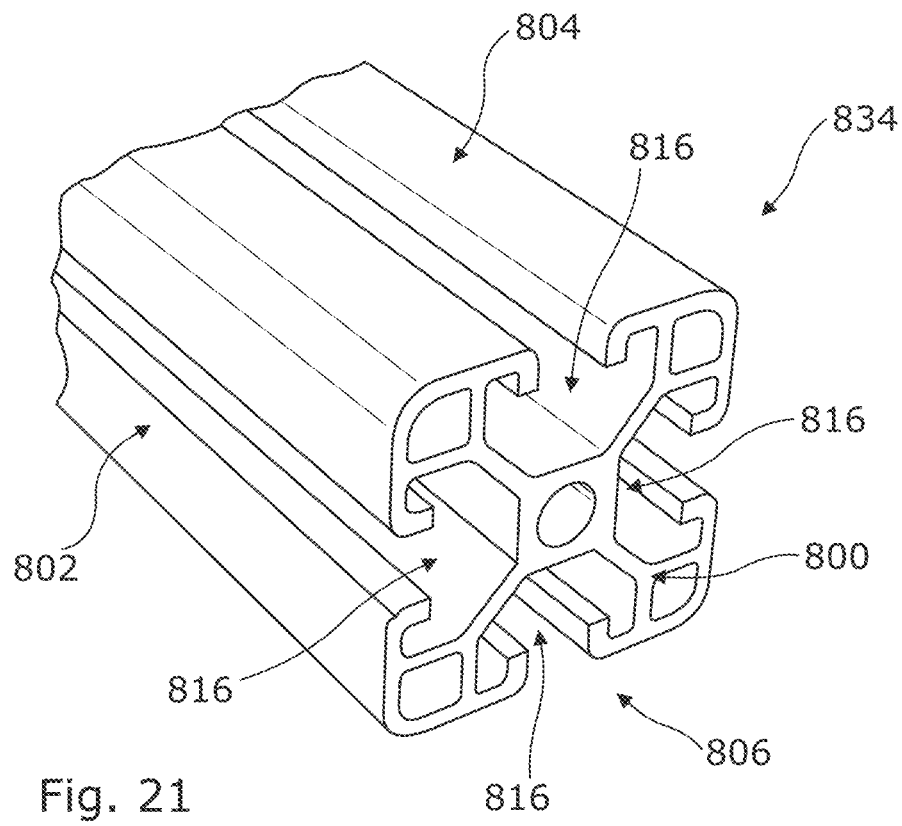
FIG. 21 is a perspective view of a portion of an alternative support member of the present disclosure.

In some embodiments, at least some of the support members may be elongate and have a generally square cross-section, having two generally square end faces 800, two generally rectangular side faces 802, and generally rectangular top and bottom faces 804 and 806, respectively, as illustrated in the support member 834 of FIG. 21. At least one side face may include a channel 816 for receiving a barrier member fixing, and in some cases each side face may include a channel 816 for receiving a barrier member fixing.

The fastenings and the connections between the support members could be of any suitable design (within the scope of the specific definitions herein).

Figure 22:
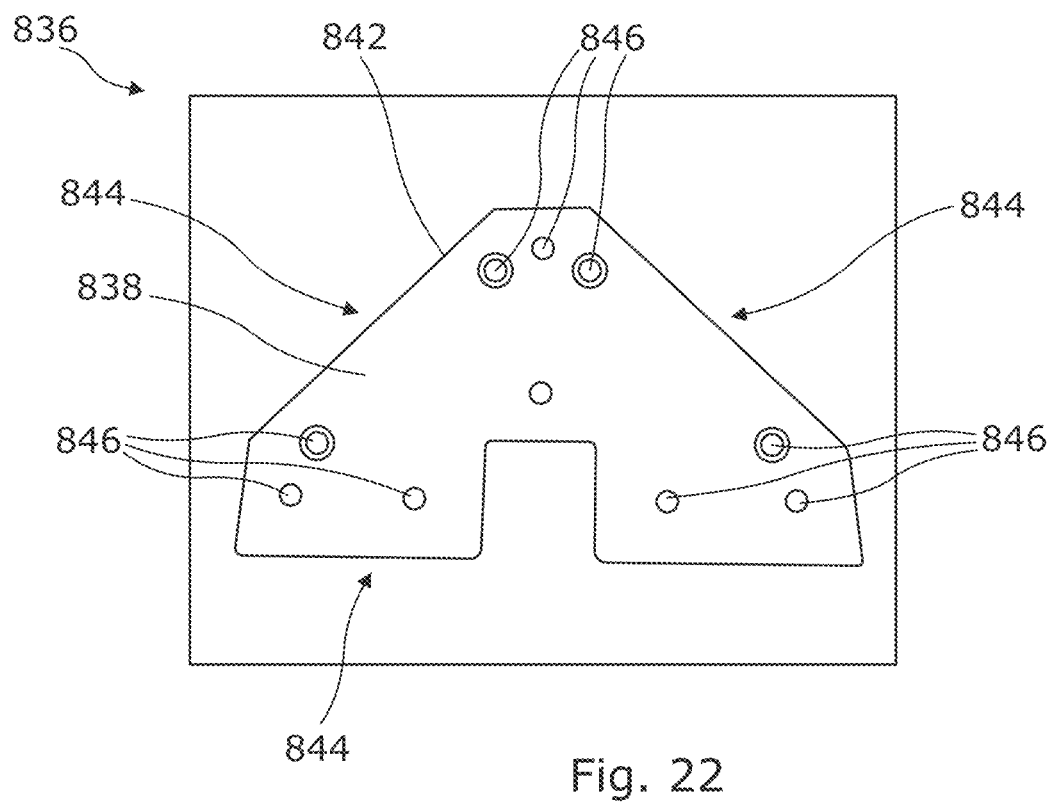
FIG. 22 is a plan view of a connection arrangement of a plant pollination control structure of the present disclosure.

FIG. 22 shows a connection arrangement or bracket 836 for connecting together support members 834. The bracket 836 is a substantially flat metal plate having a first face 838, a second face (not shown), and a peripheral edge 842 that connects the first face 838 and the second face. The bracket 836 is generally triangular in shape, having three major edges 844 that at least partially define the edges of a right-angled triangle. A plurality of openings 846, or through-holes, extend fully through a thickness of the bracket 836 defined between the first face 838 and the second face, i.e. the openings 846 penetrate the bracket. The openings 846 are configured to receive bolts 900 to allow support members 834 to be attached to the bracket 836, as will be explained. It will be understood that the number and distribution of openings 846 may vary in other embodiments, depending on the form of the complementary connection region of the support member 834.

Figure 23A:
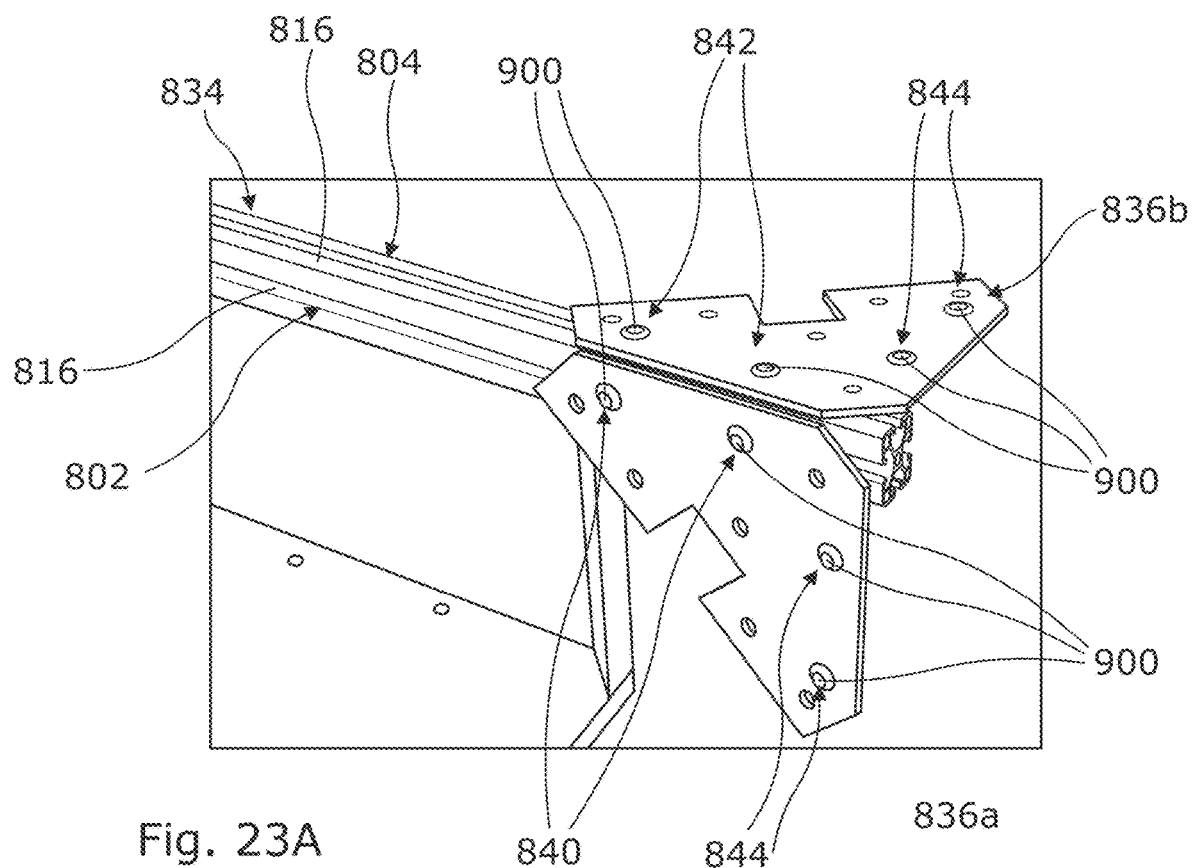
FIG. 23A and FIG. 23B illustrate how the connection arrangement of FIG. 22 can be used to connect multiple of the support members of FIG. 21.
Figure 23B:
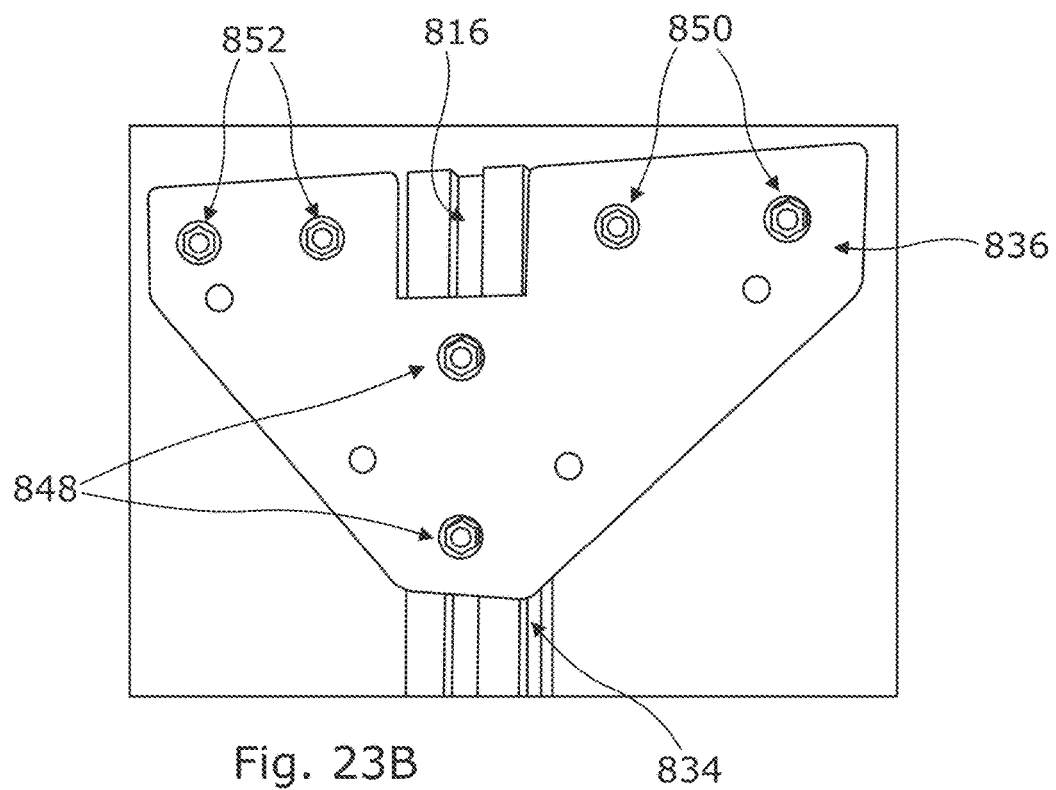

The bracket 836 allows for multiple support members 834 to be assembled in various different configurations, and can be used to connect smaller modules of a larger pollination control structure. FIGS. 23A and 23B illustrate two ways in which one or more brackets 836 may be used to connect support members 834.

Referring first to FIG. 23A, a support member 834 is attached to a first bracket 836a by means of bolts 900 that extend through openings 846 defining first attachment portions 840 of the first bracket 836a, and engage with a complementary nut (not shown) housed within the channel 816 of a side face 802 of the support member 834. The top face 804 of the support member 834 is attached at first attachment portions 842 of a second bracket 836b in a similar manner.

Although not shown in FIG. 23A, further support members 834 may be attached to the first and second brackets 836a, 836b at second attachment portions 844 in a similar manner to that already described above. In that case, the first and second brackets 836a, 836b enable three support members 834 to be assembled such that each support member 834 is arranged at 90 degrees to each of the other support members 834. Such an arrangement may be used to form a top corner of a pollination control structure, for example.

Turning now to FIG. 23B, in this arrangement a first support member 834 is attached at first attachment portions 848 of a bracket 836. Although not shown, second and third support members may be attached to the bracket 836 at second and third attachment portions 850 and 852, respectively. In that case, the first support member 834 is arranged at 90 degrees with respect to each of the second and third support members, and the second and third support members extend in the same direction as one another, such that the three support members define a T-shape.

Figure 24:
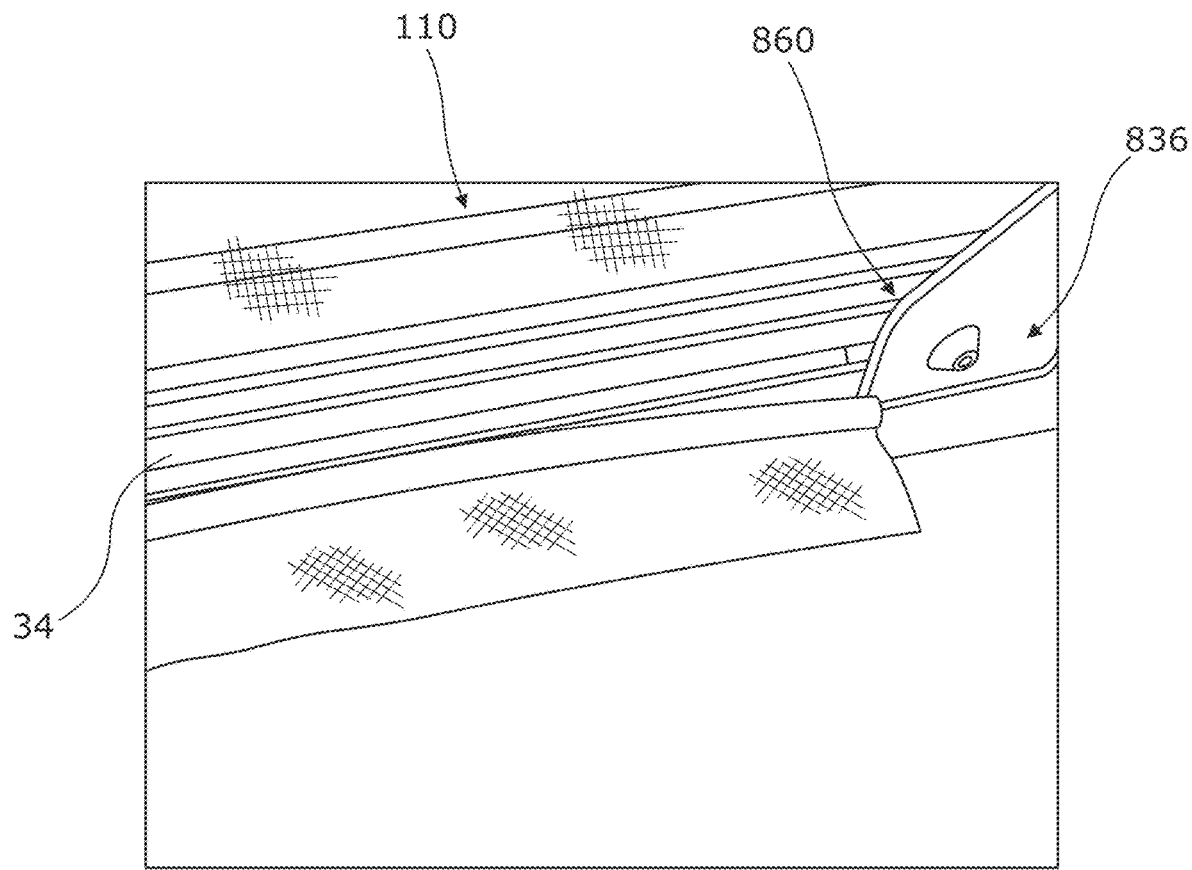
FIG. 24 is a side view of a lower corner of a plant pollination control structure of the disclosure incorporating the connection arrangement of FIG. 22.

Advantageously, the bracket 836 is a flat plate that is easy to manufacture, transport and store. A further benefit of the bracket 836, illustrated in FIG. 24, is that it does not interfere with or block use of the channels 116 at edge regions 860 of the support members 834 that it connects. In this way, barrier member fixings 122 can extend in the channels 116 to edge regions 860 of the support members 834, such that gaps between barrier member pieces 110 at corners of the structure can be avoided without the need for e.g. flaps 182 such as those shown in FIG. 20.

Any of the embodiments described could include skirt extensions.

The barrier members could include window openings and windows, door openings and doors. The windows, doors, openings and skirt extensions could be different to those shown, in number, size, location and type.

The cross sectional shapes of the bead formation and the bore could be other than circular, for example a flattened circle, an oval or a part circular shape with a flat side.

The structure could provide protection for the plant part, and could comprise a plant protection structure.

Any of the features or steps of any of the embodiments shown or described could be combined in any suitable way, within the scope of the overall disclosure of this document.

Final Remarks

There is thus provided plant pollination control structures with a number of advantages over conventional arrangements. The structures provide support to the barrier members reducing plant damage particularly for large plants or large areas of planting. The structures reduce the likelihood of damage from barrier member movement caused inadvertently by a person, an animal or by weather conditions or during fitting and removal of the barrier member.

The plant pollination control structures of the disclosure provide:

- More complete protection from windborne pollen than conventional pollination bags; for example, do not require positive pressure and hence save energy and reduce costs.
- Ease of assembly and disassembly allow the structures to be constructed only when needed, by relatively few people and easily transported.
- Allow use of barrier members amenable to creating the right internal environment that would otherwise be too weak to make structures of this size.
- The panels allow for easy replacement in the event of damage to one or more of the panels.
- Permits use of types of barrier materials currently only available on smaller pollination bags.
- Provides more complete protection and less complex set up than most state of the art solutions: e.g., polytunnels which are open at one end and typically need planning permission as they are permanent structures.
- Provides protection without requirement for positive pressure which is required for canvas tents.
- Lower cost and greater flexibility than controlled environment chambers.

The invention claimed is:

1. A pollination control structure comprising:
a support that defines a frame of the pollination control structure;
a plurality of support fixings, each support fixing being attached to or integral with the support, and;
a barrier member including a plurality of barrier member pieces;
for each barrier member piece:
each edge of the barrier member piece is releasably attached to one of the support fixings, respectively, by an intermediate fixing that offsets the barrier member piece from the support fixing,
the barrier member piece is releasably attached to each intermediate fixing, and
each intermediate fixing is releasably attached to one of the support fixings;
each of the barrier member pieces being suspended entirely within openings defined between the support fixings, each of the barrier member pieces being arranged such that the barrier member pieces do not overlap any part of the support.

2. A pollination control structure as claimed in claim 1, wherein at least one of the barrier member pieces includes releasable fastenings defined along the edges of the barrier member piece for releasably attaching the barrier member piece to the intermediate fixing.

3. A pollination control structure as claimed in claim 2, wherein the releasable fastenings include hook or loop material for releasably engaging with complementary hook or loop material of the intermediate fixing.

4. A pollination control structure as claimed in claim 1, wherein at least one of the support fixings includes a channel and at least one of the intermediate fixings includes a bead formation that slidably locates in the channel to releasably attach the intermediate fixing to the support fixing.

5. A pollination control structure as claimed in claim 1, wherein at least one of the barrier member pieces includes a non-woven material.

6. A pollination control structure as claimed in claim 1, wherein at least one of the barrier members pieces includes a different material from at least one other barrier member piece.

7. A pollination control structure as claimed in claim 1, wherein at least one of the barrier member pieces includes a skirt extension for contacting a ground surface on which the structure is assembled in a substantially continuous contact line around an interior of the structure, wherein weighting means are provided on top of, within, or integral with the skirt extensions when the structure is assembled on the ground surface.

8. A method of assembling a pollination control structure including a barrier member and a support that defines a frame of the pollination control structure, the support including a plurality of support members and the barrier member comprising a plurality of barrier member pieces, the method comprising:
assembling the support from the support members;
attaching a plurality of support fixings to the support and/or forming a plurality of support fixings integrally with the support;
attaching intermediate fixings to the support using releasable fastenings; and
for each barrier member piece, attaching each edge of the barrier member piece to at least one of the support fixings, respectively, by one of the intermediate fixings that offsets the barrier member piece from the support fixing, the barrier member piece being releasably attached to each intermediate fixing, each intermediate fixing being releasably attached to one of the support fixings, and each of the barrier member pieces being suspended entirely within an opening defined between the support fixings such that the barrier member pieces do not overlap any part of the support.

9. A kit of parts for assembling a pollination control structure, the kit of parts comprising:
a plurality of support members for forming a support that defines a frame of the pollination control structure;
a plurality of support fixings, each support fixing being attachable to or integral with the support members;
a plurality of barrier member pieces for forming a barrier member; and
a plurality of intermediate fixings configured for releasable attachment to each edge of the barrier member pieces and one of the support members, respectively, and configured to offset the barrier member piece from the support member to suspend the barrier member piece entirely within an opening defined between support members such that the barrier member piece does not overlap any part of the support.

10. A pollination control structure comprising a barrier member and a support that together define an enclosure, wherein the barrier member is supported by the support and includes at least one barrier member piece including a non-woven material, the at least one barrier member piece being suspended entirely within an opening of the support such that the at least one barrier member piece does not overlap any part of the support, wherein each edge of the at least one barrier member piece is releasably attached to the support by an intermediate fixing that offsets the at least one barrier member piece from the support.

11. A pollination control structure as claimed in claim 10, wherein each barrier member piece is releasably fixed to the support.

12. A pollination control structure as claimed in claim 10, wherein each barrier member piece has a length that is less than or equal to 2 metres and a width that is less than or equal to 2 metres.

13. A pollination control structure as claimed in claim 10, wherein at least one of the barrier member pieces is formed of a different material from at least one other barrier member piece.

14. A pollination control structure as claimed in claim 10, wherein at least one of the barrier member pieces includes a skirt extension for contacting a ground surface on which the structure is assembled in a substantially continuous contact line around an interior of the structure when the structure is assembled on the ground surface, wherein weighting means are provided on top of, within, or integral with the skirt extensions when the structure is assembled on the ground surface.

15. A pollination control structure as claimed in claim 10, wherein the support includes a plurality of body support members and a plurality of roof support member, wherein the body support members are rigid, and wherein at least one of the roof support members is more flexible than the body support members.

16. A pollination control structure as claimed in claim 15, wherein at least one of the roof support members is curved.

17. A pollination control structure as claimed in claim 10, wherein at least one of the barrier member pieces is releasably fixed to the support by an intermediate fixing that slidably locates in a channel of the support to releasably attach the barrier member piece to the support.

18. A pollination control structure as claimed in claim 17, wherein the barrier member piece is releasably attached to the intermediate fixing.

19. A pollination control structure as claimed in claim 1, wherein:
- one of the support fixings includes a first channel and a second channel; and
- the intermediate fixings of at least two of the barrier members include a bead formation, the bead formation of one of the barrier members being slidably in the first channel and the bead formation of another of the barrier members being slidably located in the second channel.

\* \* \* \* \*